United States Patent
Beckett et al.

[11] Patent Number: 5,902,791
[45] Date of Patent: May 11, 1999

[54] METALLOPROTEINASE INHIBITORS

[75] Inventors: Raymond Paul Beckett; Mark Whittaker; Andrew Miller, all of Cowley, United Kingdom

[73] Assignee: British Biotech Pharmaceuticals Limited, Oxford, United Kingdom

[21] Appl. No.: 08/676,359

[22] PCT Filed: Jan. 23, 1995

[86] PCT No.: PCT/GB95/00121

§ 371 Date: Jul. 22, 1996

§ 102(e) Date: Jul. 22, 1996

[87] PCT Pub. No.: WO95/19961

PCT Pub. Date: Jul. 27, 1995

[30] Foreign Application Priority Data

Jan. 22, 1994 [GB] United Kingdom .................. 9401416
Jul. 6, 1994 [GB] United Kingdom .................. 9413566

[51] Int. Cl.⁶ ........................ C07C 323/41; A61K 31/16
[52] U.S. Cl. ........................ 514/19; 548/477; 562/431; 562/623
[58] Field of Search .................. 562/623, 431; 548/477; 514/19

[56] References Cited

U.S. PATENT DOCUMENTS

| | | | |
|---|---|---|---|
| 3,468,936 | 9/1969 | van der Burg | 260/500.5 |
| 4,996,358 | 2/1991 | Handa et al. | 562/621 |
| 5,183,900 | 2/1993 | Galardy et al. | 548/495 |
| 5,300,674 | 4/1994 | Crimmin et al. | 560/42 |
| 5,304,549 | 4/1994 | Broadhurst et al. | 514/80 |

FOREIGN PATENT DOCUMENTS

| | | |
|---|---|---|
| 0236872 | 9/1987 | European Pat. Off. . |
| 0497192 | 1/1992 | European Pat. Off. . |
| 0575844 | 12/1993 | European Pat. Off. . |
| 2268933 | 1/1994 | United Kingdom . |
| 9402247 | 2/1994 | WIPO . |
| 9402446 | 2/1994 | WIPO . |
| WO 94/25434 | 11/1994 | WIPO . |
| WO 94/25435 | 11/1994 | WIPO . |
| 9519957 | 7/1995 | WIPO . |

*Primary Examiner*—Robert Gerstl
*Attorney, Agent, or Firm*—Hale and Dorr LLP

[57] ABSTRACT

Matrix metalloproteinase inhibiting compounds of formula (I), wherein X is a —$CO_2H$ or —CONHOH group; and one of the groups proximate to the amide bonds is a steric bulky group, showing enhanced oral absorption.

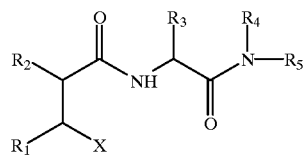

(I)

20 Claims, No Drawings

METALLOPROTEINASE INHIBITORS

The present invention relates to therapeutically active hydroxamic acid and carboxylic acid derivatives, to processes for their preparation, to pharmaceutical compositions containing them, and to the use of such compounds in medicine. In particular, the compounds are inhibitors of metalloproteinases involved in tissue degradation, and in addition are inhibitors of the release of tumour necrosis factor from cells.

BACKGROUND OF THE INVENTION

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas. However, the relative contributions of individual MMPs in any of the above disease states is not yet fully understood.

Metalloproteinases are characterised by the presence in the structure of a zinc(II) ionic site. It is now known that there exists a range of metalloproteinase enzymes that includes fibroblast collagenase (Type 1), PMN-collagenase, 72 kDa-gelatinase, 92 kDa-gelatinase, stromelysin, stromelysin-2 and PUMP-1 (L. M. Matrisian, *Trends in Genetics*, 1990, 6, 121–125). Many known MMP inhibitors are peptide derivatives, based on naturally occurring amino acids, and are analogues of the cleavage site in the collagen molecule. A recent paper by Chapman et al (J. Med. Chem. 1993, 36, 4293–4301) reports some general structure/activity findings in a series of N-carboxyalkyl peptides. Other known MMP inhibitors are less peptidic in structure, and may more properly be viewed as pseudopeptides or peptide mimetics. Such compounds usually have a functional group capable of binding to the zinc (II) site in the MMP, and known classes include those in which the zinc binding group is a hydroxamic acid, carboxylic acid, sulphydryl, and oxygenated phosphorus (eg phosphinic acid and phosphonamidate including aminophoshonic acid) groups.

Two known classes of pseudopeptide or peptide mimetic MMP inhibitors have a hydroxamic acid group and a carboxylic group respectively as their zinc binding groups. With a few exceptions, such known MMPs may be represented by the structural formula (I)

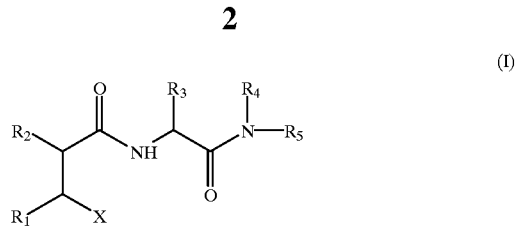

(I)

in which X is the zinc binding hydroxamic acid (—CONHOH) or carboxylic acid (—COOH) group and the groups $R_1$ to $R_5$ are variable in accordance with the specific prior art disclosures of such compounds. Examples of patent publications disclosing such structures are given below.

In such compounds, it is generally understood in the art that variation of the zinc binding group and the substituents $R_1$, $R_2$ and $R_3$ can have an appreciable effect on the relative inhibition of the metalloproteinase enzymes. The group X is thought to interact with metalloproteinase enzymes by binding to a zinc(II) ion in the active site. Generally the hydroxamic acid group is preferred over the carboxylic acid group in terms of inhibitory activity against the various metalloproteinase enzymes. However, the carboxylic acid group in combination with other substituents can provide selective inhibition of gelatinase (EP-489,577-A). The $R_1$, $R_2$ and $R_3$ groups are believed to occupy respectively the P1, P1' and P2' amino acid side chain binding sites for the natural enzyme substrate. There is evidence that a larger $R_1$ substituent can enhance activity against stromelysin, and that a $(C_1-C_6)$alkyl group (such as iso-butyl) at $R_2$ may be preferred for activity against collagenase whilst a phenylalkyl group (such as phenylpropyl) at $R_2$ may provide selectivity for gelatinase over the other metalloproteinases.

Pseudopeptide or peptide mimetic MMP inhibitors of formula (I) with potent in vitro activities are known, but are generally poorly absorbed following oral administration. Although it is known that a number of factors can influence oral absorption (such as aqueous solubility, pKa, log P and molecular weight). the design of pseudopeptide enzyme inhibitors with high oral absorption is far from straightforward. Finding a combination of $R_1$, $R_2$, $R_3$, $R_4$ or $R_5$ substituents that permits a good balance of intrinsic level of activity, water solubility, oral absorbtion, and pharmacokinetic properties is a continuing problem in the art, since those properties can vary in an unpredictable way as the substituents $R_1$–$R_5$ are varied. Identifying hydroxamic and carboxylic acid-based MMP inhibitors having such properties remains a much sought after goal in the art.

Tumour necrosis factor (herein referred to as "TNF") is a cytokine which is produced initially as a cell-associated 28 kD precursor. It is released as an active, 17 kD form, which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Compounds which inhibit the production or action of TNF are therefore thought to be potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Since excessive TNF production has been noted in several diseases or conditions also characterised by MMP-mediated tissue degradation, compounds which inhibit both MMPs and TNF production may have particular advantages in the treatment or prophylaxis of diseases or conditions in which both mechanisms are involved.

Recently, WO 93/20047 disclosed a class of hydroxamic acid based MMP inhibitors which also are active in inhibiting TNF production.

As mentioned above, MMP inhibitors have been proposed with hydroxamic acid or carboxylic acid zinc binding groups. The following patent publications disclose hydroxamic acid-based MMP inhibitors:

| US 4599361 | (Searle) |
| EP-A-0236872 | (Roche) |
| EP-A-0274453 | (Bellon) |
| WO 90/05716 | (British Bio-technology) |
| WO 90/05719 | (British Bio-technology) |
| WO 91/02716 | (British Bio-technology) |
| EP-A-0489577 | (Celltech) |
| EP-A-0489579 | (Celltech) |
| EP-A-0497192 | (Roche) |
| WO 92/13831 | (British Bio-technology) |
| WO 92/17460 | (SmithKline Beecham) |
| WO 92/22523 | (Research Corporation Technologies) |
| WO 93/09090 | (Yamanouchi) |
| WO 93/09097 | (Sankyo) |
| WO 93/20047 | (British Bio-technology) |
| WO 93/24449 | (Celltech) |
| WO 93/24475 | (Celltech) |
| EP-A-0574758 | (Roche) |

The following patent publications disclose carboxylic acid-based MMP inhibitors.

| EP-A-0489577 | (Celltech) |
| EP-A-0489579 | (Celltech) |
| WO 93/24449 | (Celltech) |
| WO 93/24475 | (Celltech) |

BRIEF DESCRIPTION OF THE INVENTION

Recent studies comparing the absorption of peptides with their N-methylated analogues suggest that hydrogen bonding potential is a determinant of in vivo absorption (M. S. Karis et al., *Pharmaceutical Research*, 1991, 8, 1477–1481). It is argued that peptides with lower hydrogen bonding potential are more readily absorbed because there is a lower cost in terms of desolvation energy on absorbtion into the intestinal mucosa. It was the hypothesis of the inventors of the present invention that appropriate modification of the groups $R_3$, $R_4$ and R5, in structures of formula (I) that are proximate to the amide bonds, could lead to metalloproteinase inhibitors with enhanced oral absorption. In particular, it was thought that the introduction of steric bulk proximate to the amide bonds could reduce their hydrogen bonding potential. It was a further hypothesis of the inventors that the introduction of heteroatoms (such as oxygen, sulphur or fluorine) in an appropriate position in $R_3$ or $R_4$ such that they form intermolecular hydrogen bonds with the N-H of one of the amide groups could reduce the desolvation energy for absorption.

The present invention therefore makes available MMP inhibitors of the general structure (I) above with a hydroxamic acid of carboxylic acid zinc binding group X, designed in accordance with those hypotheses. The new class includes compounds with appropriate aqueous solubility, pKa, log P and molecular weight for good oral absorption, which maintain good inhibitory potencies against the various metalloproteinase enzymes, and which have other desirable pharmacokinetic and physicochemical properties.

A further advantage of certain compounds of the present invention is that they inhibit the production of the pro-inflammatory cytokine TNF.

Of the patent publications listed above relating to hydroxamic and carboxylic acid based MMP inhibitors, the only disclosure of specific compounds with a bulky $R_3$ group appears to be EP-A-0497192 (Roche). In that case the bulky group is t-butyl. Others of the listed publications refer generally to lower alkyl or $C_{1-6}$ alkyl groups in the $R_3$ position, without specifying steric bulk. None of the listed publications disclose compounds with $R_3$ or $R_4$ groups selected for their ability to form intramolecular hydrogen bonds with the adjacent amide N-H.

DETAILED DESCRIPTION OF THE INVENTION

The present invention provides compounds of general formula I

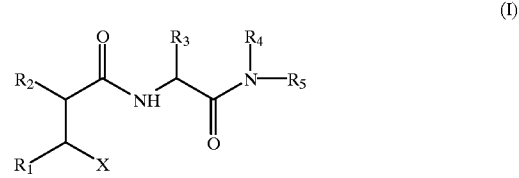

wherein
X is a —CO$_2$H or —CONHOH group;
$R_1$ is hydrogen; (C$_1$–C$_6$)alkyl; (C$_2$–C$_6$)alkenyl; phenyl; substituted phenyl; phenyl (C$_1$–C$_6$)alkyl); substituted phenyl(C$_1$–C$_6$)alkyl; heterocyclyl; substituted heterocyclyl; heterocyclyl(C$_1$–C$_6$)alkyl; substituted heterocyclyl(C$_1$–C$_6$)alkyl; a group BSO$_n$A- wherein n is 0, 1 or 2 and B is hydrogen or a (C$_1$–C$_6$) alkyl, phenyl, substituted phenyl, heterocyclyl, (C$_1$–C$_6$)acyl, phenacyl or substituted phenacyl group, and A represents (C$_1$–C$_6$)alkyl; amino; protected amino; acylamino; OH; SH; (C$_1$–C$_6$)alkoxy; (C$_1$–C$_6$)alkylamino; di-(C$_1$–C$_6$)alkylamino; (C$_1$–C$_6$)alkylthio; aryl (C$_1$–C$_6$) alkyl; amino(C$_1$–C$_6$)alkyl; hydroxy(C$_1$–C$_6$)alkyl, mercapto(C$_1$–C$_6$)alkyl or carboxy(C$_1$–C$_6$)alkyl wherein the amino-, hydroxy-, mercapto- or carboxyl-group are optionally protected or the carboxyl-group amidated; lower alkyl substituted by carbamoyl, mono (lower alkyl)carbamoyl, di(lower alkyl)carbamoyl, di(lower alkyl)amino, or carboxy-lower alkanoylamino;
$R_2$ is a (C$_1$–C$_6$)alkyl, (C$_2$–C$_6$)alkenyl, (C$_2$–C$_6$)alkynyl, phenyl(C$_1$–C$_6$)alkyl, heteroaryl(C$_1$–C$_6$)alkyl, cycloalkyl(C$_1$–C$_6$)alkyl or cycloalkenyl(C$_1$–C$_6$) alkyl group, any one of which may be optionally substituted by one or more substituents selected from (C$_1$–C$_6$)

alkyl, —O($C_1$–$C_6$)alkyl, —S($C_1$–$C_6$)alkyl, halo and cyano (—CN);

$R_3$ is either
(a) a hydrocarbon group —$CR_6R_7R_8$ in which each of $R_6$, $R_7$ and $R_8$ is independently ($C_1$–$C_6$)alkyl, ($C_2$–$C_6$)alkenyl, ($C_2$–$C_6$)alkynyl, phenyl($C_1$–$C_6$) alkyl, ($C_3$–$C_8$)cycloalkyl; or $R_6$ and $R_7$ together with the carbon atom to which they are attached form a 3 to 8 membered cycloalkyl or a 5- to 6-membered heterocyclic ring; or $R_6$, $R_7$ and $R_8$ together with the carbon atom to which they are attached form a tricyclic ring (for example adamantyl);
provided that when each of $R_6$, $R_7$, $R_8$ is independently ($C_1$–$C_6$) alkyl or ($C_2$–$C_6$)alkenyl then the total number of carbon atoms in the group $R_3$ exceeds 6;
or (b) a group —$CR_9R_{10}R_{11}$ in which
$R_9$ and $R_{10}$ are each independently ($C_1$–$C_6$)alkyl, ($C_2$–$C_6$)alkenyl, ($C_2$–$C_6$)alkynyl, phenyl($C_1$–$C_6$) alkyl, or a group as defined for $R_{11}$ below other than hydrogen, or $R_9$ and $R_{10}$ together with the carbon atom to which they are attached form a 3 to 8 membered cycloalkyl or a 3- to 8-membered heterocyclic ring; and
$R_{11}$ is hydrogen, OH, SH, halogen, CN, $CO_2H$, ($C_1$–$C_4$)perfluoroalkyl, $CH_2OH$, $CO_2$($C_1$–$C_6$) alkyl, or a —O($C_1$–$C_6$) alkyl, —O($C_2$–$C_6$) alkenyl, —S($C_1$–$C_6$) alkyl, —SO($C_1$–$C_6$)alkyl, —$SO_2$($C_1$–$C_6$) alkyl, —S($C_2$–$C_6$) alkenyl, —SO ($C_2$–$C_6$)alkenyl, —$SO_2$($C_2$–$C_6$)alkenyl; or a group —Q—W wherein Q represents a bond or —O—, —S—, —SO— or —$SO_2$- and W represents a phenyl, phenylalkyl, ($C_3$–$C_8$)cycloalkyl, ($C_3$–$C_8$)cycloalkylalkyl, ($C_4$–$C_8$)cycloalkenyl, ($C_4$–$C_8$)cycloalkenylalkyl, heteroaryl or heteroarylalkyl group, which group W may optionally be substituted by one or more substituents independently selected from, hydroxyl, halogen, CN, $CO_2H$, $CO_2$($C_1$–$C_6$)alkyl, $CONH_2$, CONH ($C_1$–$C_6$)alkyl, CONH($C_1$–$C_6$alkyl)$_2$, CHO, $CH_2OH$, ($C_1$–$C_4$)perfluoroalkyl, O($C_1$–$C_6$)alkyl, S($C_1$–$C_6$)alkyl, SO($C_1$–$C_6$)alkyl, $SO_2$($C_1$–$C_6$) alkyl, $NO_2$, $NH_2$, NH($C_1$–$C_6$)alkyl, N(($C_1$–$C_6$) alkyl)$_2$, NHCO($C_1$–$C_6$)alkyl, ($C_1$–$C_6$)alkyl, ($C_2$–$C_6$)alkenyl, ($C_2$–$C_6$)alkynyl, ($C_3$–$C_8$) cycloalkyl, ($C_4$–$C_8$)cycloalkenyl, phenyl or benzyl;
provided that when both of $R_9$ and $R_{10}$ are independently ($C_1$–$C_6$)alkyl, ($C_2$–$C_6$)alkenyl, ($C_2$–$C_6$) alkynyl, or phenyl($C_1$–$C_6$)alkyl then $R_{11}$ is other than hydrogen;
$R_4$ is hydrogen, ($C_1$–$C_6$)alkyl, ($C_1$–$C_4$)perfluoroalkyl or a group D-($C_1$–$C_6$ alkyl)- wherein D represents hydroxy, ($C_1$–$C_6$)alkoxy, ($C_1$–$C_6$)alkylthio, acylamino, optionally substituted phenyl or heteroaryl, —$NH_2$, or mono- or di-($C_1$–$C_6$ alkyl amino;
$R_5$ is hydrogen or a ($C_1$–$C_6$)alkyl group;
or a salt hydrate or solvate thereof.

As used herein the term "($C_1$–$C_6$)alkyl" or "lower alkyl" means a straight or branched chain alkyl moiety having from 1 to 6 carbon atoms, including for example, methyl, ethyl, n-propyl, isopropyl, n-butyl, isobutyl, sec-butyl, t-butyl, pentyl and hexyl.

The term "($C_2$–$C_6$)alkenyl" means a straight or branched chain alkenyl moiety having from 2 to 6 carbon atoms and having in addition one double bond of either E or Z stereochemistry where applicable. This term would include, for example, vinyl, 1-propenyl, 1- and 2-butenyl and 2-methyl-2-propenyl.

The term "cycloalkyl" means a saturated alicyclic moiety having from 3–8 carbon atoms and includes, for example, cyclopropyl, cyclobutyl, cyclopentyl, cyclohexyl, cycloheptyl and cyclooctyl.

The term "cycloalkenyl" means an unsaturated alicyclic moiety having from 3–8 carbon atoms and includes, for example, cyclopropenyl, cyclobutenyl, cyclopentenyl, cyclohexenyl, cycloheptenyl and cyclooctenyl. In the case of cycloalkenyl rings of from 5–8 carbon atoms, the ring may contain more than one double bond.

The unqualified term "heterocyclyl" or "heterocyclic" means (i) a 5–7 membered heterocyclic ring containing one or more heteroatoms selected from S, N and O, and optionally fused to a benzene ring, including for example, pyrrolyl, furyl, thienyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin-4-yl, 3-methyl-2,5-dioxo-1-imidazolidinyl and 3,4,4-trimethyl-2,5-dioxo-1-imidazolidinyl, or (ii) a naphthothalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group.

The term "5- or 6-membered heterocyclic ring" means such rings having 5 or 6 atoms in the ring, wherein the heteroatom(s) may be one or more nitrogen, oxygen or sulphur atoms, and includes heterocycles containing nitrogen, oxygen, or sulphur alone or containing two nitrogen atoms, a nitrogen and an oxygen atom, a nitrogen and a sulphur atom, two nitrogen atoms and an oxygen atom, two nitrogen atoms and a sulphur.

The "heteroaryl" means a 5–7 membered substituted or unsubstituted aromatic heterocycle containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

Unless otherwise specified in the context in which it occurs, the term "substituted" as applied to any moiety herein means substituted with up to four substituents, each of which independently may be $C_1$–$C_6$ alkoxy, hydroxy, thio, $C_1$–$C_6$ alkylthio, amino, halo (including fluoro, chloro, bromo and iodo), trifluoromethyl, nitro, —COOH, —$CONH_2$ or —$CONHR^A$ wherein $R^A$ is a $C_1$–$C_6$ alkyl group or the residue of a natural alpha-amino acid.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereoisomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:

C atom carrying the $R_1$ and X group —S,
C atom carrying the $R_2$ group —R,
C atom carrying the $R_3$ group —S, but mixtures in which the above configurations predominate are also contemplated.

As previously stated, the compounds of the invention are principally distinguished from the compounds disclosed in the prior art patent publications listed above by the identity of the group $R_3$. Accordingly, the groups $R_1$, $R_2$, $R_4$, and $R_5$ may be any of the groups which have been disclosed in the corresponding positions of compounds disclosed in any of those prior art patent publications listed above.

More specifically with respect to the groups $R_1$, $R_2$, $R_3$, $R_4$ and $R_5$ in compounds of the invention:

Examples of particular $R_1$ groups include hydrogen, methyl, ethyl, hydroxyl, allyl, thienylmethylsulphanyl, thienylmethylsulphinyl, thienylmethylsulphonyl and phthalimidomethyl. Presently preferred are compounds in which $R_1$ is hydrogen, hydroxyl, allyl or phthalimidomethyl.

Examples of particular $R_2$ groups include iso-butyl, n-pentyl, n-hexyl, n-heptyl, n-octyl, n-nonyl, n-decyl, cyclohexylpropyl, phenylpropyl, 4-chlorophenylpropyl, 4-methylphenylpropyl, 4-methoxyphenylpropyl, phenylbutyl, propyloxymethyl and propylsulphanyl. Presently preferred are compounds in which $R_2$ is isobutyl, n-heptyl, or phenylpropyl.

$R_3$ groups include:
—C($C_2$–$C_6$ alkyl)$_3$;
—CH($C_1$–$C_4$ perfluoroalkyl)$_2$;
—C($C_1$–$C_4$ perfluoroalkyl)$_3$; and
—C($C_1$–$C_6$ alkyl)$_2R_{11}$ or a 3 to 8 membered cycloalkyl group substituted by ($C_1$–$C_6$)alkyl or $R_{11}$ at the α-position, wherein
$R_{11}$ is —OH, —SH, halogen, ($C_1$–$C_4$)perfluoroalkyl, —CH$_2$OH, —CO$_2$H, —CO$_2$($C_1$–$C_6$)alkyl, optionally substituted phenyl or optionally substituted heteroaryl, —O($C_1$–$C_6$ alkyl), —S($C_1$–$C_6$ alkyl), —SO($C_1$–$C_6$ alkyl), —SO$_2$($C_1$–$C_6$ alkyl), —OPh, —OCH$_2$Ph, —SPh, —SOPh, —SO$_2$Ph, —SCH$_2$Ph, —SOCH$_2$Ph, or —SO$_2$CH$_2$Ph, cyclohexylmethylsulphanyl, cyclohexylmethylsulphinyl, or cyclohexylmethylsulphonyl in which any of the foregoing Ph (phenyl) or cyclohexyl groups may be substituted, for example by —OH or —O($C_1$–$C_6$ alkyl) or halogen.

Examples of particular $R_3$ groups include 1,1-diethylprop-1-yl, 1-cyclopropyl-ethyl, adamant-1-yl, 2-fluoroprop-2-yl, 1,1,1,3,3,3-hexafluoroprop-2-yl, 2-hydroxyprop-2-yl, 2-mercaptoprop-2-yl, 2-methoxyprop-2-yl, 2-carboxyprop-2-yl, 2-methoxycarbonylprop-2-yl, 2-(2-methoxyethoxymethoxy)prop-2-yl, 2-(tetrahydropyran-4-yl)prop-2-yl, 2-(tetrahydrofuran-2-yl)prop-2-yl, 1-hydroxy-cyclopent-1-yl, 2-methylsulphanyl -prop-2-yl, 2-methylsulphinylprop-2-yl, 2-methylsulphonylprop-2-yl, 2-benzylsulphanylprop-2-yl, 2-benzylsulphinyl-prop-2-yl, 2-benzylsulphonylprop-2-yl, 2-(4-methoxybenzylsulphanyl)prop-2-yl, 2-(4-methoxybenzylsulphinyl)prop-2-yl, 2-(4-methoxybenzylsulphonyl) prop-2-yl, 2-cyclohexylmethylsulphanyl-prop-2-yl, cyclohexylmethylsulphinyl-prop-2-yl, cyclohexylmethylsulphanyl-prop-2-yl, diphenylmethyl or 2-phenylprop-2-yl. Particularly preferred are compounds in which $R_3$ is 2-fluoroprop-2-yl, 2-methylsulphanylprop-2-yl, 2-methylsulphinyl-prop-2-yl, 2-methylsulphonylprop-2-yl, 2-mercaptoprop-2-yl, 2-benzylsulphanyl-prop-2-yl, 2-benzylsulphinylprop-2-yl, cyclohexylmethylsulphanylprop-2-yl and 2-(4-methoxybenzylsulphinyl)prop-2-yl.

$R_4$ may for example be $C_1$–$C_6$ alkyl, ($C_1$–$C_4$) perfluoroalkyl or a group D-($C_1$–$C_6$ alkyl) wherein D represents hydroxy, ($C_1$–$C_6$)alkoxy, ($C_{1-C6}$) alkylsulphanyl, acylamino, optionally substituted phenyl or heteroaryl. Examples of particular $R_4$ groups include methyl, ethyl, propyl, n-butyl, t-butyl, hydroxyethyl, hydroxypropyl, 2,2-dimethyl-3-hydroxypropyl, hydroxybutyl, methoxyethyl, ethoxyethyl, methoxypropyl, 2,2-dimethyl-3-methoxypropyl, 2,2-dimethyl-3-ethoxypropyl, 2-ethylthioethyl, 2-acetoxyethyl, N-acetylaminoethyl, 3-(2-pyrrolidone)propyl, optionally substituted phenylethyl, phenylpropyl, phenylbutyl and phenylpentyl. Presently preferred are compounds in which $R_4$ is methyl, t-butyl or benzyl. Presently most preferred are compounds in which $R_4$ is methyl.

Examples of particular $R_5$ groups include hydrogen, methyl and ethyl. Presently preferred are compounds in which $R_5$ is hydrogen.

Specific compounds of the invention which are at present preferred for their oral bioavailability are:

2S-Hydroxy 3R-[2-(4-methoxybenzylsulphinyl)-2-methyl-1S-(methylcarbamoyl)-propylcarbamoyl]-5-methyl-hexanohydroxamic acid 2S-Hydroxy-3R-[1S-(methylcarbamoyl)-2-benzylsulphanyl-2-methylpropylcarbamoyl]-5-methyl-hexanohydroxamic acid 2S-Hydroxy-3R-[2-methylthio-2-methyl-1S-(methylcarbamoyl)propylcarbamoyl]-5-methyl-hexanohydroxamic acid 3R-[2-Benzylsulphanyl-2-methyl-1S-(methylcarbamoyl) propylcarbamoyl]-2S-hydroxy-6-phenyl-hexanohydroxamic acid 2S-Hydroxy-3R-[1S-(methylcarbamoyl)-2-fluoro-2-methyl-propylcarbamoyl]-5-methyl-hexanohydroxamic acid 3R-[2-Benzylsulphanyl-2-methyl-1S-(methylcarbamoyl)-propylcarbamoyl]-5-methyl-2S-propen-2-yl-hexanohydroxamic acid 3R-[2-Benzylsulphinyl-2-methyl-1S-(methylcarbamoyl) propylcarbamoyl]-2S-hydroxy-5-methyl-hexanohydroxamic acid 3R-[2-Cyclohexylmethylsulphanyl-2-methyl-1S-(methylcarbamoyl)propylcarbamoyl]-5-methyl-2S-hydroxy-hexanohydroxamic acid 3R-[2-Cyclohexylmethylsulphanyl-2-methyl-1S-(methylcarbamoyl)propylcarbamoyl]-5-methyl-2S-propen-2-yl-hexanohydroxamic acid 3R-[2-Methylsulphinyl-2-methyl-1S-(methylcarbamoyl) propylcarbamoyl]-5-methyl-2S-propen-2-yl-hexanohydroxamic acid 3R-[2-Methylsulphonyl-2-methyl-1S-(methylcarbamoyl) propylcarbamoyl]-5-methyl-2S-propen-2-yl-hexanohydroxamic acid 3R-[2-Mercapto-2-methyl-1S-(methylcarbamoyl)-propylcarbamoyl]-5-methyl-2S-propen-2-yl-hexanohydroxamic acid and salts, solvates and hydrates thereof.

Additional interesting compounds of the invention are:
3R-[1S-(Methylcarbamoyl)-2-benzylsulphanyl-2-methyl-propylcarbamoyl]-5-methyl-hexanohydroxamic acid 3R-[1S-Benzylcarbamoyl-(1-methylcyclopropyl)
  methylcarbamoyl]-5-methyl-hexanohydroxamic acid
3R-[2-Benzylsulphanyl-1S-(methylcarbamoyl)-2-
  methyl-propylcarbamoyl]-6-phenyl-
  hexanohydroxamic acid
2S-Hydroxy 3R-[2-(4-methoxybenzylsulphanyl)-2-
  methyl-1S-(methylcarbamoyl)-propylcarbamoyl]-5-
  methyl-hexanohydroxamic acid
2S-Hydroxy-3R-[1S-(methylcarbamoyl)-2-
  trifluoromethyl-3,3,3-trifluoropropylcarbamoyl]-5-
  methyl-hexanohydroxamic acid
3R-[2,2-Diphenyl-1S-(methylcarbamoyl)
  ethylcarbamoyl]-2S-hydroxy-5-methyl-
  hexanohydroxamic acid
2S-Hydroxy-3R-[2-hydroxy-1RS-(methylcarbamoyl)-2-
  methyl-propylcarbamoyl]-5-methyl-
  hexanohydroxamic acid
2S-Hydroxy-3R-[2,2-diethyl-1S-(methylcarbamoyl)-
  butylcarbamoy-5-methyl-hexanohydroxamic acid
2S-Hydroxy-3R-[1S-methylcarbamoyl-2-methyl-2-
  phenylpropylcarbamoyl]-5-methyl-hexanohydroxamic
  acid
2S-Hydroxy-3R-[1S-tert-butylcarbamoyl-2-
  benzylsulphanyl-2-methyl-propylcarbamoyl]-5-
  methyl-hexanohydroxamic acid
2S-Hydroxy-3R-[1S-(methylcarbamoyl)-2-mercapto-2-
  methylpropylcarbamoyl]-5-methyl-hexanohydroxamic
  acid
2S-Hydroxy-3R-[S-(methylcarbamoyl)-adamant-1-
  ylmethylcarbamoyl]-5-methyl-hexanohydroxamic acid
2S-Hydroxy-3R-[2-methoxy-1S-(methylcarbamoyl)-2-
  methyl-propylcarbamoyl]-5-methyl-
  hexanohydroxamic acid
2S-Hydroxy-3R-[2-methoxycarbonyl-1S-(-
  methylcarbamoyl)-2-methylpropylcarbamoyl]-5-
  methyl-hexanohydroxamic acid
3R-[2-Methylthio-2-methyl-1S-(methylcarbamoyl)
  propylcarbamoyl]-5-methyl-2S-propen-2-yl-
  hexanohydroxamic acid
3R-[2,2-Diphenyl-1S-(methylcarbamoyl)-
  propylcarbamoyl]-5-methyl-2S-propen-2-yl-
  hexanohydroxamic acid
3R-[2,2-Diethyl-1S-(methylcarbamoyl)-
  butylcarbamoyl]-5-methyl-2S-propen-2-yl-
  hexanohydroxamic acid
3R-[2-Benzylsulphanyl-2-methyl-1S-
  (methylcarbamoyl)-propylcarbamoyl]-5-methyl-2S-
  phthalimidomethyl-hexanohydroxamic acid
3R-[2-Benzylsulphonyl-2-methyl-1S-(methylcarbamoyl)
  propylcarbamoyl]-2S-hydroxy-5-methyl-
  hexanohydroxamic acid
2S-Hydroxy 3R-[2-(4-methoxybenzylsulphonyl)-2-
  methyl-1S-(methylcarbamoyl)-propylcarbamoyl]-5-
  methyl-hexanohydroxamic acid
2S-Hydroxy 3R-[2-methylsulphinyl-2-methyl-1S-
  (methylcarbamoyl)-propylcarbamoyl]-5-methyl-
  hexanohydroxamic acid
2S-Hydroxy 3R-[2-methylsulphonyl-2-methyl-1S-
  (methylcarbamoyl)-propylcarbamoyl]-5-methyl-
  hexanohydroxamic acid
3R-[2-Benzylsulphinyl-2-methyl-1S-methylcarbamoyl-
  propylcarbamoyl]-5-methyl-2S-propen-2-yl-
  hexanohydroxamic acid 3R-[2-Benzylsulphanyl-2-methyl-1S-(methylcarbamoyl)
  propylcarbamoyl]-2S-hydroxy-6-phenyl-hexanoic acid
  and salts, solvates and hydrates thereof.

Compounds according to the present invention in which X is a hydroxamic acid group —CONHOH may be prepared from corresponding compounds of the invention in which X is a carboxylic acid group —COOH or from the corresponding protected hydroxamic acid derivatives. That process, which forms another aspect of the invention, comprises:

(a) causing an acid of general formula (II)

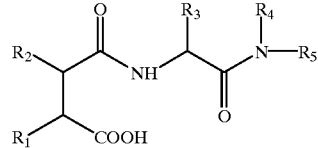

(II)

or an activated derivative thereof to react with hydroxylamine, O-protected hydroxylamine, or an N,O-diprotected hydroxylamine, or a salt thereof, $R_1$, $R_2$, $R_3$, $R_4$, and $R_5$ being as defined in general formula (I) except that any substituents in $R_1$, $R_2$, $R_3$, $R_4$, and $R_5$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, $R_4$, and $R_5$; or (b) deprotecting a diprotected hydroxamic acid derivative of formula (IIb)

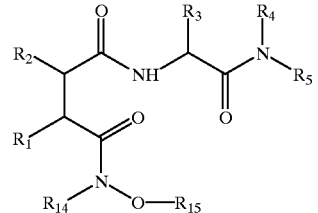

(IIb)

in which $R_1$, $R_2$, $R_3$, $R_4$, and $R_5$ are as defined in general formula (I), $R_{14}$ is an amino protecting group and $R_{15}$ is a hydroxyl protecting group.

For method (a) conversion of (II) to an activated intermediate such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in method (a) above include O-benzylhydroxylamine, O-4-methoxybenzylhydroxylamine, O-trimethylsilylhydroxylamine, and O-tert-butoxycarbonylhydroxylamine.

Examples of O,N-diprotected hydroxylamines for use in method (a) above include N,O-bis(benzyl)hydroxylamine, N,O-bis(4-methoxybenzyl)hydroxylamine, N-tert-butoxycarbonyl-O-tert-butyldimethylsilylhydroxylamine, N-tert-butoxycarbonyl-O-tetrahydropyranylhydroxylamine, and N,O-bis(tert-butoxycarbonyl)hydroxylamine.

For method (b) suitable protecting groups $R_{14}$ and $R_{15}$ are benzyl and substituted benzyl (eg 4-methoxybenzyl). Such protecting groups may be removed by hydrogenolysis, while the 4-methoxybenzyl group may also be removed by acid hydrolysis.

In method (a) in the special case where $R_1$ in compound (I) is hydroxy, a particularly useful technique may be reaction of hydroxylamine with a dioxalone of formula (IIa):

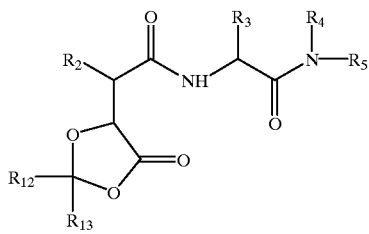

(IIa)

wherein the groups $R_{12}$ and $R_3$ are derived from a dioxalone forming reagent, and may be, for example, hydrogen, alkyl, phenyl or substituted phenyl. The dioxalone ring is opened on reaction with hydroxylamine to give the required hydroxamic acid derivative of formula (I).

Compounds according to the present invention in which X is a carboxylic acid group —COOH may be prepared by a process comprising: coupling an acid of formula (III) or an activated derivative thereof with an amine of formula (IV)

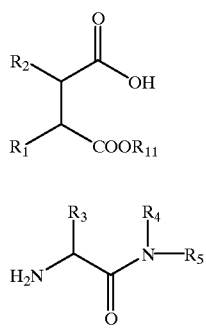

(III)

(IV)

wherein $R_1$ $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, and $R_{11}$ represents a hydroxy protecting group, and subsequently removing the protecting group $R_{11}$ and any protecting groups from $R_1$ $R_2$, $R_3$, $R_4$, and $R_5$.

Compounds of formula (IIb) may be prepared by a process comprising: causing an acid of formula (IIIa) or an activated derivative thereof to react with an amine of formula (IV)

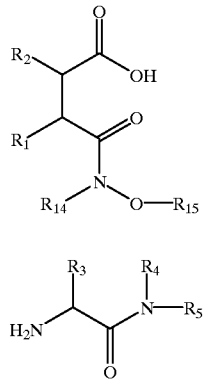

(IIIa)

(IV)

wherein $R_1$, $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, $R_{14}$ is an amino protecting group and $R_{15}$ is a hydroxyl protecting group as referred to in connection with formula (IIb) above, and subsequently removing any protecting groups from $R_1$, $R_2$, $R_3$, $R_4$, and $R_5$.

Active derivatives of acids (III) and (IIIa) include activated esters such as the pentafluorophenyl ester, acid anhydrides and acid halides, eg chlorides. Suitable hydroxy protecting groups $R_{11}$ may be selected from those known in the art. Amine intermediates of formula (IV) are either known compounds or may be prepared from known amino acid starting materials using standard methods and by analogy with the specific preparative examples herein.

In the special case where $R_1$ in compound (III) or (IIIa) is hydroxy, it too may be protected during the coupling of compounds (III) or (IIIa) and (IV). In the case where $R_1$ is hydroxy in compound (III) a particularly useful technique may be simultaneous protection of the two hydroxy groups as a dioxalone of formula (V):

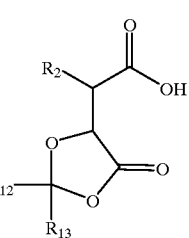

(V)

wherein the groups $R_{12}$ and $R_{13}$ are derived from a dioxalone forming reagent, and may be, for example, hydrogen, alkyl, phenyl or substituted phenyl.

As mentioned above, compounds of formula (I) are useful in human or veterinary medicine since they are active as inhibitors of MMPs, and a further advantage lies in their ability to inhibit the release of tumour necrosis factor (TNF) from cells. Accordingly in another aspect, this invention concerns:

(i) a method of management (by which is meant treatment or prophylaxis) of diseases or conditions mediated by MMPs and/or TNF in mammals, in particular in humans, which method comprises administering to the mammal an effective amount of a compound as defined with respect to formula (I) above, or a pharmaceutically acceptable salt thereof; and (ii) a compound as defined with respect to formula (I) for use in human or veterinary medicine, particularly in the management (by which is meant treatment or prophylaxis) of diseases or conditions mediated by MMPs and/or TNF; and (iii) the use of a compound as defined with respect to formula (I) in the preparation of an agent for the management (by which is meant treatment or prophylaxis) of diseases or conditions mediated by MMPs and/or TNF.

Diseases or conditions mediated by MMPs include those involving tissue breakdown such as bone resorption, inflammatory and neuroinflammatory diseases, dermatological conditions, solid tumour growth and tumour invasion by secondary metastases, and angiogenesis dependent diseases, in particular rheumatoid arthritis, osteoarthritis, periodontitis, gingivitis, corneal ulceration, solid tumour growth and tumour invasion by secondary metastases, neovascular glaucoma, multiple sclerosis, and psoriasis. Diseases or conditions mediated by TNF include inflammation, fever, cardiovascular effects, haemorrhage, coagulation and acute phase response, cachexia and anorexia, acute infections, shock states, graft versus host reactions and autoimmune disease.

In a further aspect of the invention there is provided a pharmaceutical or veterinary composition comprising a compound of formula (I) together with a pharmaceutically or veterinarily acceptable excipient or carrier. Included within this aspect of the invention is a pharmaceutical or veterinary composition comprising a compound of formula (I) together with a pharmaceutically or veterinarily acceptable excipient or carrier, characterised in that the composition is adapted for oral administration.

One or more compounds of general formula (I) may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives. for example methyl or propyl p-hydroxybenzoate or sorbic acid, and if desired conventional flavouring or colouring agents.

The dosage unit involved in oral administration may contain from about 1 to 250 mg, preferably from about 25 to 250 mg of a compound of the invention. A suitable daily dose for a mammal may vary widely depending on the condition of the patient. However, a dose of a compound of general formula I of about 0.1 to 300 mg/kg body weight, particularly from about 1 to 100 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint. The daily dosage for a 70 kg mammal may be in the range 10 mgs to 1 gram.

The examples which follow illustrate embodiments of the invention but are not intended to limit the scope in any way. The amino acids used in the examples were commercially available or were prepared by procedures known to one skilled in the art.

The following abbreviations have been used throughout:

| | |
|---|---|
| DCHA | Dicyclohexylamine |
| DIPE | Diisopropyl ether |
| DMF | N,N-Dimethylformamide |
| HOBt | 1-Hydroxybenzotriazole |
| LDA | Lithium diisopropylamide |
| mCPBA | m-Chloroperbenzoic acid |
| NMM | N-Methylmorpholine |
| THF | Tetrahydrofuran |
| TFA | Trifluoroacetic acid |
| TLC | Thin layer chromatography |
| EDC | N-Ethyl-N'-(3-dimethylaminopropyl)carbodiimide hydrochloride |

$^1$H and $^{13}$C NMR spectra were recorded using a Bruker AC 250E spectrometer at 250.1 and 62.9 MHz, respectively. Elemental microanalyses were performed by CHN Analysis Ltd. (Alpha House, Countesthorpe Road, South Wigston, Leicester LE8 2PJ, UK) or Medac Ltd. (Department of Chemistry, Brunel University, Uxbridge, Middlesex UB8 3PH).

EXAMPLE 1

3R-[1S-Methylcarbamoyl-2-benzylsulphanyl-2-methyl-propylcarbamoyl]-5-methylhexanohydroxamic acid

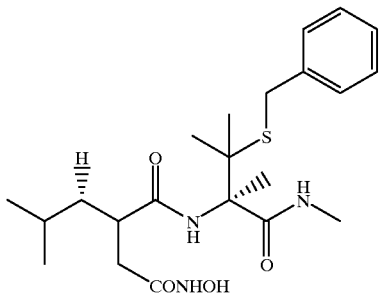

STEP A:
N-(4-Methylpentanoyl)-4S-phenylmethyl-oxazolidin-2-one

A dry 500 ml flask equipped with a magnetic stirrer was charged with 4S-phenylmethyl-oxazolidin-2-one (17.72 g, 100 mmol), this was capped with a rubber septum and flushed with nitrogen. Anhydrous THF (300 ml) was added via a cannula and the resulting solution was cooled to −78° C. in an acetone/dry-ice bath.

A solution of 1.47M n-butyllithium in hexane (68.4 ml, 101 mmol) was transferred via cannula to a dry, septum-stoppered 100 ml dropping funnel. This was added dropwise to the THF solution over 10 minutes.

4-Methylvaleric acid chloride (14.80 g, 110 mmol) was added in one portion by syringe after completion of the addition of n-butyllithium. The resulting solution was stirred at −78° C. for 30 minutes and then allowed to warm to ambient temperature over 30 minutes. Excess acid chloride was quenched by the addition of aq. ammonium chloride (60 ml) and the bulk of the solvent was removed under reduced pressure. The resulting slurry was extracted with dichloromethane (2×80 ml). The combined organic extracts were washed with 1M sodium hydroxide (75 ml), brine (75 ml), dried (anhydrous sodium sulphate) and filtered. The solvent was removed to yield a yellow oil (29.20 g, including residual solvent) which was used directly in Step B.
$^1$H-NMR: δ (CDCl$_3$), 7.34–7.19 (5H, m). 4.73–4.63 (1H, m), 4.25–4.16 (2H, m), 3.30 (1H, dd, J=3.3 Hz), 3.05–2.85 (2H, m), 2.78 (1H, dd, J=9.5 Hz), 1.76 −1.53 (3H, m) and 0.97 (6H, d, J=6.2 Hz).

STEP B:
N-(4-(tert-Butyl)-2R-isobutyl-butan-1,4-dioyl)-4S-phenylmethyl-oxazolidin-2-one N-(4-Methylpentanoyl)-4S-phenylmethyl-oxazolidin-2-one (20 g, 72.6 mmol) was placed in a dry 1 liter 3-necked flask to which was added dry THF (400 ml). The mixture was kept under a stream of argon and cooled to −78° C. (dry ice/acetone). Sodium bis(trimethyl)silylamide (1M solution in THF, 72.6 ml, 72.6 mmol) was added dropwise through a dropping funnel. After stirring for 20 minutes, tert-butyl bromoacetate (21.02 g, 15.8 ml, 109 mmol) was added dropwise over 1 minute, to give an orange solution. The mixture was kept at −78° C. and allowed to warm to −50° C. over 2 hours (after which time it turned pink). The reaction was then quenched by adding acetic acid (10.90 g, 10.4 ml, 182 mmol) in ether (50 ml) at −50° C., whereupon the solution became colourless. The solvent was removed under reduced pressure and the resulting slurry was partitioned between ethyl acetate and brine. The ethyl acetate layer was washed once with brine and the original brine layer was back-extracted with ethyl acetate. The combined organic layers were dried and the solvent removed, giving a yellow oil which crystallised on cooling overnight to yield the title compound as a crystalline solid (21.36 g, 76%).
$^1$H-NMR; δ (CDCl$_3$), 7.38–7.24 (5H, m), 4.67 (1H, m), 4.27 (1H, m), 4.18–4.16 (2H, m), 3.36 (1H, dd, J=3.3 Hz), 2.72 (1H, dd, J=2.3 Hz), 2.49 (1H, dd, J=4.6 Hz), 1.72–1.24 (3H, m), 1.44 (9H, s) and 0.91–0.96 (6H, dd, J=4.5 Hz). $[α]^{25}_D$=+66.9° (c=1, MeOH).

STEP C:
2R-Isobutyl-butan-1,4-dioic acid-4-tert-butyl ester

N-(4-(tert-Butyl)-2R-isobutyl-butan-1,4-dioyl)-4S-phenylmethyl-oxazolidin-2-one (15.30 g, 39 mmol) was placed in a 1 liter flask with a stirrer bar and to it was added a mixture of THF (600 ml) and water (150 ml). The solution was stirred and cooled to 0° C. (ice/acetone bath) then 60% aq. hydrogen peroxide (4.5 ml, 157 mmol) was added via syringe over 5 minutes, followed by lithium hydroxide (2.65 g, 63 mmol) in 100 ml water. The reaction mixture was stirred for 1 h at 0° C. TLC analysis (10% methanol in dichloromethane) showed complete reaction (product gave a yellow spot on TLC on staining with bromocresol green and heating). The reaction mixture was quenched with sodium nitrite (10.88 g, 157 mmol), the final pH was 12–13. THF was removed in-vacuo and the aqueous layer was extracted with dichloromethane (3×200 ml) to recover the chiral auxiliary. The organic extracts were dried (anhydrous magnesium sulphate), filtered and the solvent removed in-vacuo and the resulting solid chiral auxiliary (7.05 g, 39 mmol, 100%) recrystallised from ethyl acetate-hexane (2:1). $[α]^{25}_D$=−13.0° (c=1, MeOH)

The aqueous layer was cooled in an ice bath and acidified to pH 5–6 with 2M hydrochloric acid. The resulting cloudy solution was extracted with ethyl acetate (4×200 ml), readjusting the pH to 5–6 in between extractions. The combined organic extracts were dried over magnesium sulphate, filtered and the solvent was removed to yield the title compound as a pale yellow oil (8.21 g, 91%). $^1$H-NMR; δ (CDCl$_3$), 2.85 (1H, m), 2.59 (1H, dd, J=16, 9 Hz), 2.38 (1H, dd, J=16, 5 Hz), 1.64 (1H, m), 1.43 (9H, s), 1.28 (1H, m) and 0.93 (6H, dd, J=7, 8 Hz). $[α]^{25}_D$=+10.4° (c=1, MeOH).

STEP D:
3R-[2-Benzylsulphanyl-1S-(methylcarbamoyl)-2-methyl-propylcarbamoyl]-5-methyl-hexanoic acid tert-butyl ester 2R-lsobutyl-butan-1,4-dioic acid-4-tert-butyl ester (8.83 g, 38.4 mmol) was dissolved in DMF (300 ml) and the solution was cooled in an ice bath. HOBt (6.22 g, 46.0 mmol), EDC (8.82 g, 46.0 mmol) and S-benzyl-L-penicillamide-N-methylamide (19.41g, 76.7 mmol) were added and the reaction mixture was stirred overnight at room temperature with stirring. TLC analysis indicated that all of the carboxylic acid precursor had been consumed. The solvent was removed and the residue was taken up in ethyl acetate and washed successively with water, sat, sodium hydrogen carbonate, 1M hydrochloric acid and brine. The organic phase was dried (anhydrous magnesium sulphate), filtered and evaporated to leave the product as a yellow foam (18.14 g, 98%). $^1$H-NMR; δ ((CD$_3$)$_2$SO), 7.99 (1H, m), 7.83 (1H, m), 7.21–7.01 (5H, br m), 4.48 (1H, d, J=9.7 Hz), 3.68 (2H, s), 2.76 (1H, m), 2.45 (3H, d, J=4.4 Hz), 2.30 (1H, m), 2.05 (1H, dd, J=6.9, 16.0 Hz), 1.40–1.20 (3H, br m), 1.21 (12H, s), 1.12 (3H, s), 0.72 (3H, d, J=6.2 Hz) and 0.66 (3H, d, J=6.1 Hz.)

STEP E:
3R-[2-Benzylsulphanyl-1S-(methylcarbamoyl)-2-methyl-propylcarbamoyl]-5-methyl-hexanoic acid 3R-[2-Benzylsulphanyl-1S-(methylcarbamoyl)-2-methyl-propylcarbamoyl]-5-methyl-hexanoic acid tert-butyl ester (5.575, 11.6 mmol) was dissolved in dichloromethane (50 ml) and TFA (50 ml) and the solution was stored overnight at 4° C. The solvents were removed in vacuo, the residue was dissolved in ethyl acetate and washed twice with water to remove residual TFA. The organic phase was dried (anhydrous magnesium sulphate), filtered and evaporated to leave a white foam (4.98 g, including residual solvent). $^1$H-NMR; δ (CDCl$_3$), 7.49 (1H, d, J=9.0 Hz), 7.37–7.17 (5H, br m), 6.44 (1H, m), 4.67 (1H, d, J=9.0 Hz), 3.81 (2H, m), 2.87 (1H, m), 2.75 (3H, d, J=4.7 Hz), 2.68 (1H, m), 2.45 (1H, dd, J=4.1, 1.69 Hz), 1.67–1.43 (2H, br m), 1.40 (3H, s), 1.35–1.23 (4H, s and m), 0.89 (3H, d, J=6.5 Hz) and 0.86 (3H, d, J=6.3 Hz).

STEP F:

3R-[2-Benzylsulphanyl-1S-(methylcarbamoyl)-2-methyl-propylcarbamoyl]-5-methyl-hexanohydroxamic acid 3R-[2-Benzylsulphanyl-1S-(methylcarbamoyl)-2-methyl-propylcarbamoyl]-5-methyl-hexanoic acid (4.98 g, 11.6 mmol) was dissolved in DMF (75 ml) and the solution was cooled in an ice bath. HOBt (1.88 g, 17.4 mmol) and EDC (2.67 g, 13.9 mmol) were added and the mixture was stirred at 0° C. for 1 h then at room temperature for 2 h. The solution was cooled back to 0° C. during the addition of hydroxylamine hydrochloride (1.21 g, 17.4 mmol), then stirred overnight at room temperature. The solvent was removed under reduced pressure to leave an oil which was triturated with diethyl ether (120 ml)/water (120 ml) and left to stand in an ice bath for 1.5 h. The resulting precipitate was collected by filtration and washed with cold diethyl ether. The desired product (1.12 g, 24%) was obtained as a white solid following column chromatography (acid-washed silica gel, 5% methanol in dichloromethane). m.p. 69–70° C. $^1$H-NMR; δ (CD$_3$OD), 7.96 (1H, m), 7.15 (5H, m), 4.52 (1H, m), 3.72 (2H, s), 2.83 (1H, m), 2.65 (3H, s), 2.28 (1H, m), 2.08 (1H, m), 1.34 (3H, s), 1.27 (3H, s), 1.20 (1H, m), 0.81 (3H, d, J=6.5 Hz) and 0.77 (3H, d, J=6.4 Hz). $^{13}$C-NMR; δ (CD$_3$OD), 177.0, 172.2, 170.6, 139.2, 130.3, 129.4, 60.0, 42.0, 37.2, 34.1, 27.1, 26.5, 26.2, 25.8, 23.5 and 22.5. IR (KBr disc); V$_{max}$, 3288, 2958, 1644, 1533, 1464 and 1368 cm$^{-1}$. Found: C 58.90, H 7.85, N 9.64%; C$_{21}$H$_{33}$N$_3$O$_4$S.0.3 H$_2$O requires C 58.80, H 7.89, N 9.80%.

The following additional compound was prepared according to the methods of Example 1:

EXAMPLE 2

3R-[1RS-Benzylcarbamoyl-(1-methylcyclopropyl) methylcarbamoyl]-5-methylhexanohydroxamic acid

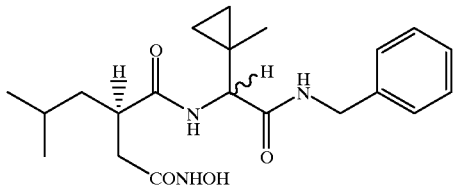

Mixture of diastereoisomers (1:1)

White solid. m.p. 175–180° C. $^1$H-NMR; δ (CD$_3$OD), 7.06–7.24 (5H, m), 4.38–4.05 (3H, br m), 2.78 (1H, m), 2.21 (1H, m), 2.05 (1H, m), 1.77 (1H, m), 1.55–1.25 (3H, br m), 1.12–0.96 (2H, br m) and 0.89–0.71 (12H, m). $^{13}$C-NMR; δ (CD$_3$OD), 177.3, 173.3, 173.6, 170.5, 139.8, 129.5, 129.3, 128.6, 128.2, 127.9, 59.3, 58.7, 44.0, 42.5, 42.2, 42.1, 38.3, 37.8, 37.1, 27.2, 27.0, 26.0, 23.6, 22.4, 15.9, 15.2, 11.8 and 11.2.

EXAMPLE 3

3R-[2-Benzylsulphanyl-1S-(methylcarbamoyl)-2-methyl-propylcarbamoyl]-6-phenyl-hexanohydroxamic acid

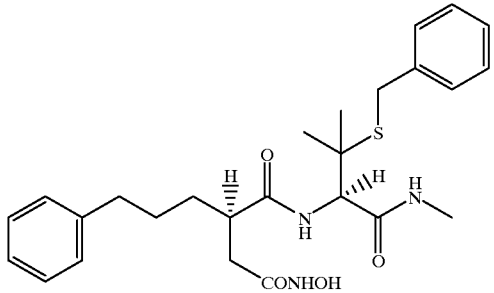

White crystalline solid. m.p. 165–167° C. $^1$H-NMR; δ ((CD$_3$)$_2$SO), 8.56 (1H, s), 8.02–7.93 (1H, m), 7.88 (1H, d, J=9.5 Hz), 7.21–6.95 (10H, m), 4.48 (1H, d, J=9.6 Hz), 3.65 (2H, s), 2.48–2.23 (2H, m), 2.43 (3H, d, J=4.5 Hz), 2.07 (1H, dd, J=5.9, 14.5 Hz), 1.93 (1H, dd, J=8.3, 14.4 Hz), 1.42–1.17 (4H, m), 1.22 (3H, s) and 1.14 (3H, s). $^{13}$C-NMR; δ ((CD$_3$)$_2$SO), 173.9, 169.6, 167.5, 142.2, 137.9, 129.2, 128.3, 128.2, 126.7, 125.6, 57.7, 48.5, 41.2, 35.4, 35.2, 32.3, 31.4, 28.6, 25.8, 25.4 and 25.1. IR (KBr disc); v$_{max}$, 3215, 2931, 1647 and 1518 cm$^{-1}$.

EXAMPLE 4

2S-Hydroxy-3R-[1RS-(methylcarbamoyl)-2-fluoro-2-methyl-propylcarbamoyl]-5-methyl-hexanohydroxamic acid

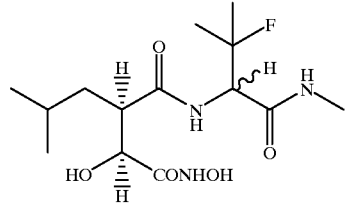

STEP A:

2S-Hydroxy-3R-isobutenyl-butan-1,4-dioic acid diisopropyl ester

2S-Hydroxybutan-1,4-dioic acid diisopropyl ester (50 g, 230 mmol) was added to a solution of LDA [from N,N-diisopropylamine (80 ml, 570 mmol) and 10M n-butyllithium (48.1 ml, 481 mmol)] in dry THF (500 ml) whilst maintaining the temperature at −70° C. When addition was complete the reaction was warmed to −15° C. and stirred for 8 hours. The reaction mixture was cooled to −70° C. and methallyl iodide (46 g, 252 mmol) was added slowly, ensuring that the temperature did not exceed −65° C. The mixture was warmed to −40° C. and stirred for 18 hours before quenching at −15° C. with citric acid. The organic layer was separated and washed with 10% sodium hydrogen carbonate solution (500 ml) and brine (300 ml) then dried (anhydrous magnesium sulphate). The solution was filtered and concentrated in vacuo to give a brown oil (64 g) which was purified by column chromatography (silica gel, 1 kg, gradient elution with 20 to 35% diethyl ether in hexane). The desired product was isolated as a colourless oil (30.9 g, 49%) which was found to be a 17:1 mixture of diastereoisomers by NMR. $^1$H-NMR; δ (CDCl$_3$, major diastereoisomer), 5.06

(1H, septet, J=6.3 Hz), 4.97 (1H, septet, J=6.3 Hz), 4.78 (2H, d, J=7.1 Hz), 4.16 (1H, m), 3.20 (1H, d, J=6.2 Hz), 3.00 (1H, m), 2.50 (1H, dd, J=7.0, 14.5 Hz), 2.35 (1H, dd, J=8.7, 14.4 Hz), 1.72 (3H, s) and 1.24–1.16 (12H, 2m).

STEP B:
2S-Hydroxy-3R-isobutyl-butan-1,4-dioic acid diisopropyl ester

2S-Hydroxy-3R-isobutenyl-butan-1,4-dioic acid diisopropyl ester (7.14 g, 26.2 mmol) was dissolved in ethanol (80 ml), and stirred overnight with 10% palladium on charcoal catalyst (1.0 g) under an atmosphere of hydrogen. The catalyst was removed by filtration and the filtrate was evaporated to dryness to leave the product as a clear oil (7.03 g, 98%). $^1$H-NMR; δ (CDCl$_3$), 5.06 (1H, septet, J=6.3 Hz), 4.97 (1H, septet, J=6.3 Hz), 4.17 (1H, br s,), 3.24 (1H, br s), 2.83 (1H, m), 1.68 (2H, m,), 1.44 (1H, m), 1.24 (6H, d, J=6.2 Hz), 1.18 (6H, d, J=6.2 Hz) and 0.89 (6H, m).

STEP C:
2S-Hydroxy-3R-isobutyl-butan-1,4-dioic acid

2S-Hydroxy-3R-isobutyl-butan-1.4-dioic acid diisopropyl ester (7.0 g, 25.6 mmol) was dissolved in dioxane (15 ml) and water (1.5 ml), a solution of potassium hydroxide (4.29 g) in water (22 ml) was added and the mixture was heated at 90° C. overnight. The solution was allowed to cool and then passed through an ion exchange resin (Dowex 50X4-400, 200 ml) and evaporated to yield the title compound (4.82 g, 99%). $^1$H-NMR; δ (CDCl$_3$), 8.70 (2H, br s), 4.32 (1H, br s), 3.10 (1H, m), 1.85–1.55 (3H, m) and 0.96 (6H, m).

STEP D:
2R-(2,2-Dimethyl-4-oxo-1,3-dioxalan-5S-yl)-4-methylpentanoic acid

2S-Hydroxy-3R-isobutyl-butan-1,4-dioic acid (5.19 g, 27.3 mmol) was dissolved in 2,2-dimethoxypropane (150 ml) and DMF (40 ml) and stirred overnight at 30° C. in the presence of a catalytic amount of p-toluene sulphonic acid. The solvent was removed to give the title compound contaminated with solvent (6.87 g, crude). $^1$H-NMR; δ (CDCl$_3$), 4.41 (1H, d, J=4.8 Hz), 2.91 (1H, m), 1.69 (3H, m), 1.54 (3H, s), 1.48 (3H, s) and 0.88 (6H, m).

STEP E:
2R-(2,2-Dimethyl-4-oxo-1,3-dioxalan-5S-yl)-4-methyl pentanoic acid pentafluorophenyl ester 2R-(2,2-Dimethyl-4-oxo-1,3-dioxalan-5S-yl)-4-methylpentanoic acid (558 mg, 2.4 mmol) was taken up in dichloromethane (10 ml) and cooled to 0° C. before adding pentafluorophenol (670 mg, 3.6 mmol) and EDC (560 mg, 2.9 mmol). The reaction was stirred at 0° C. for 2 hours then the solution was washed with 1M sodium carbonate (50 ml) and brine (20 ml). The organic layer was dried (magnesium sulphate), filtered, evaporated to dryness and purified by column chromatography (silica gel, dichloromethane) to give the activated ester (552 mg, 58%). $^1$H-NMR; δ (CDCl$_3$), 4.57 (1H, d, J=6.5 Hz), 3.32 (1H, m), 1.86 (3H, m), 1.67 (3H, s), 1.58 (3H, s) and 1.03 (6H, m).

STEP F:
N$^α$-tert-Butyloxycarbonyl-2RS-3-fluorovaline

To a cooled (0° C.) solution of 2RS-3-fluorovaline (3.0 g, 22.2 mmol) in DMF (30 ml) was added triethylamine (6.5 ml, 46.7 mmol) and di-tert-butyl-dicarbonate (5.3 g, 24.4 mmol) with stirring. The mixture was allowed to warm to room temperature then stirred overnight. The solvent was removed under reduced pressure and the residue was taken up in dichloromethane and washed successively with 1M hydrochloric acid and brine. The organic phase was dried (anhydrous magnesium sulphate), filtered and evaporated to leave a yellow oil which was used without further purification. $^1$H-NMR; δ (CDCl$_3$), 8.31, (1H, br s), 5.40 (1H, d, J=9.8 Hz), 4.41 (1H, m), 1.52 (3H, s), 1.49 (9H, s) and 1.41 (3H, s).

STEP G:
N$^α$-tert-Butyloxycarbonyl-2RS-3-fluorovaline-N-methylamide

N$^α$-tert-Butyloxycarbonyl-2RS-3-fluorovaline (1.91 g, 8.13 mmol) was dissolved in DMF (30 ml) and the solution was cooled to 0° C. and stirred during the addition of pentafluorophenol (2.24 g, 12.2 mmol), followed by EDC (1.87 g, 9.75 mmol). The mixture was allowed to warm to room temperature, stirred for a further 1 hour then cooled back to 0° C. Methylamine (2 ml, 16.3 mmol) was added dropwise and the mixture was warmed to room temperature then stirred for a further 48 hours. The solvent was removed under reduced pressure and the residue was dissolved in dichloromethane and washed successively with 1M hydrochloric acid, 1M sodium carbonate and finally with brine before drying over anhydrous magnesium sulphate. The organic phase was filtered and evaporated to an oil which was purified by column chromatography (silica gel, 2% methanol in dichloromethane).

Yield: 863 mg (43%). $^1$H-NMR: δ (CDCl$_3$), 6.31 (1H, br s), 5.59 (1H, d, J=9.6 Hz). 4.31 (1H, m), 2.83 (3H, d, J=6.2 Hz) and 1.51–1.21 (15H, m).

STEP H:
2R,S-3-Fluorovaline-N-methylamide

N$^α$-tert-Butyloxycarbonyl-2R,S-3-fluorovaline-N-methylamide was dissolved in dichloromethane (40 ml) and TFA (30 ml) and the solution was stored at 4° C. overnight. The solvents were removed under reduced pressure and the residue was dissolved in methanol (15 ml) and water (5 ml). Dowex TM 1X8 ion exchange resin (OH— form) was added until the pH of the solution was ca. 7. The resin was removed by filtration and the solvents were removed under reduced pressure to leave an oil which was used in the next step without further purification. Yield: 775 mg (515 mg max. i.e. contained solvent). $^1$H-NMR; δ (CD$_3$OD), 3.71 (1H, d, J=10.2 Hz), 2.78 (3H, s), 1.46 (3H, d, J=6.4 Hz) and 1.38 (3H, d, J=6.2 Hz).

STEP I:
N$^α$-[2R-(2,2-Dimethyl-4-oxo-1,3-dioxalan-5S-yl)-4-methylpentanoyl]-2R,S-3-fluorovaline-N-methylamide 2R,S-3-Fluorovaline-N-methylamide (515 mg, 3.5 mmol) was dissolved in DMF (40 ml) and cooled to 0° C. before the addition of 2R-(2,2-dimethyl-4-oxo-1,3-dioxalan-5S-yl)-4-methyl-pentanoic acid pentafluorophenyl ester (1.45 g, 3.65 mmol). The solution was stirred for 10 minutes at 0° C., then for 4 days at 35° C. The solvent was removed under reduced pressure and the residue was dissolved in dichloromethane and washed successively with 1M sodium carbonate and brine. The organic phase was dried (anhydrous magnesium sulphate), filtered and evaporated under reduced pressure to leave a solid which was recrystallised from ethyl acetate-hexane. Yield (580 mg, 46%). $^1$H-NMR; 67 (CDCl$_3$, 1:1 mixture of diastereoisomers), 6.81 (1H, m), 6.18 (1H, br s), 4.62 (1H, m), 4.48 (1H, dd, J=5.9, 6.0 Hz), 2.84 (3H, d, J=4.8 Hz), 2.82 (1H, m), 1.70 and 1.61 (6H, 2s), 1.66 and 1.54 (6H, 2s), 1.45 (3H, d, J$_{HF}$=22.8 Hz), 1.34 (3H, J$_{HF}$= 21.8 Hz) and 0.94 (6H, d, J=6.1 Hz).

STEP J:
2S-Hydroxy-3R-[1S-(methylcarbamoyl)-2-fluoro-2-methyl-propylcarbamoyl]-5-methyl-hexanohydroxamic acid Hydroxylamine hydrochloride (448 g, 6.5 mmol) was dissolved in methanol (10 ml), anhydrous sodium methoxide (348 mg, 6.5 mmol) was added and the mixture was stirred for 2 hours at room temperature. The residual solid was removed by filtration and the filtrate was cooled to 0° C. during portionwise addition of N$^\alpha$-[2R-(2,2-Dimethyl-4-oxo-1,3-dioxalan-5S-yl)-4-methylpentanoyl]-2R,S-3-fluorovaline-N-methylamide (580 mg, 1.6 mmol). The solution was stirred for 1 hour at 0° C., DMF (8 ml) was added to aid dissolution of the solids then the solution was stirred overnight at room temperature. TLC analysis indicated that starting material remained so the mixture was evaporated to small volume and added to a fresh batch of hydroxylamine, prepared as above, then stirred overnight, whereupon the reaction went to completion. The solvent was removed under reduced pressure and the residue was purified by column chromatography (acid-washed silica, gradient elution with 10–20% methanol in dichloromethane) followed by recrystallisation of the separate fractions from methanol-DIPE to afford the following:

| Batch 1 | 87 mg, 3:2 mixture of diastereoisomers |
| Batch 2 | 65 mg, 5.1 mixture of diastereoisomers |
| Batch 3 | 54 mg, single diastereisomer |
| Batch 4 | 35 mg, 1:1 mixture from mother liquors of batch 1 |

Total yield: 46%.
Batch 3: single isomer (SRR)
White solid. m.p. 180–181° C. $^1$H NMR; δ (CD$_3$OD), 4.47 (1H, d, J=16.9 Hz), 3.94 (1H, d, J=7.4 Hz), 2.88 (1H, m), 2.68 (3H, s), 1.56 (1H, m), 1.44 (4H, d and m, J=5.3 Hz), 1.35 (3H, d, J=5.2 Hz), 1.13 (1H, m) and 0.88 (6H, t, J=6.9 Hz). $^{13}$C NMR; δ (CD$_3$OD), 175.9, 171.4, 171.3, 159.9, 97.3, 94.5, 73.4, 61.3, 60.9, 38.6, 27.0, 26.3, 25.2, 25.1, 24.7, 23.8, 22.0 and 21.5.
Batch 4: 1:1 mixture of SRR and SRS isomers
White solid. m.p. 190–192° C. $^1$H-NMR; δ (CD$_3$OD), 4.55 (0.5H, d, J=15.9 Hz), 4.47 (0.5H, d, J=16.7 Hz), 4.08 (0.5H, d, J=7.1 Hz), 3.96 (0.5H, d, J=7.4 Hz), 2.88 (1H, m), 2.71 (1.5H, s), 2.68 (1.5H, s), 1.60 (1H, m), 1.51–1.32 (7H, br m), 1.13 (1H, m) and 0.88 (6H, m).

The following additional compounds were prepared as single diastereoisomers (unless otherwise stated) according to the methods of Example 4, starting from the appropriate amino acids:

EXAMPLE 5

2S-Hydroxy-3R-[1S-(methylcarbamoyl)-2-benzylsulphanyl-2-methylpropylcarbamoyl]-5-methyl-hexanohydroxamic acid

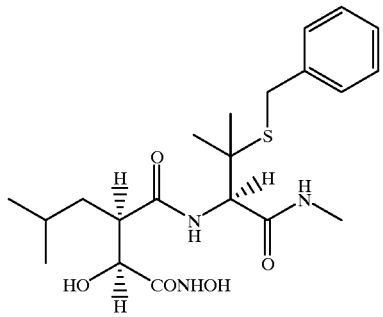

White solid. m.p. 153–154° C. $^1$H-NMR; δ (CD$_3$OD), 7.27 (5H, m), 4.51 (1H, s), 4.07 (1H, d, J=5.1 Hz), 3.78 (2H, s), 2.83 (1H, m), 2.72 (3H, s), 1.60 (2H, m), 1.40 (3H, s), 1.35 (4H, s+m), 0.90 (3H, d, J=6.2 Hz) and 0.84 (3H, d, J=6.2Hz). $^{13}$C NMR; δ (CD$_3$OD), 175.4, 172.2, 171.5, 139.0, 130.3, 129.4, 127.9, 72.8, 60.4, 39.9, 34.1, 26.9, 26.8, 26.3, 26.0, 23.6 and 22.3.

EXAMPLE 6

2S-Hydroxy 3R-[2-(4-methoxybenzylsulphanyl)-2-methyl-1S-(methylcarbamoyl)-propylcarbamoyl]-5-methyl-hexanohydroxamic acid

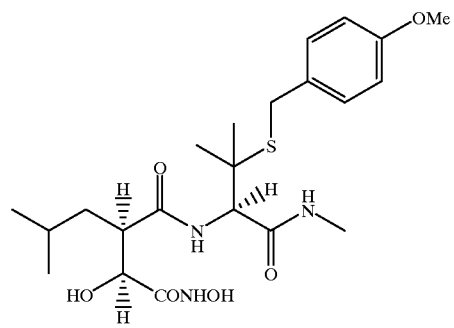

White solid. m.p. 158–159 ° C. 1H NMR; δ (CD$_3$OD), 7.18 (2H, d, J=8.6 Hz), 6.78 (2H, d, J=8.6 Hz), 4.5 (1H, s), 4.07 (1H, d, J=5.3 Hz), 3.71 (5H, s), 2.83 (1H, m), 2.72 (3H, s), 1.60 (2H, m), 1.39 (3H, s), 1.34 (3H, s), 1.29 (1H, m), 0.90 (3H, d, J=6.4 Hz) and 0.83 (3H, d, J=6.4 Hz). $^{13}$C NMR; 8 (CD$_3$OD), 175.4, 172.2, 171.5, 160.2, 131.4, 130.7, 114.9, 72.8, 60.4, 55.7, 39.9, 33.4, 26.8, 26.4, 26.0, 23.6 and 22.4. Found: C 54.26, H 7.41, N 8.85%; C$_{22}$H$_{35}$N$_3$O$_6$S. 1.0 H$_2$O requires C 54.19, H 7.65, N 8.62%.

EXAMPLE 7

2S-Hydroxy-3R-[2-methylthio-2-methyl-1S-(methylcarbamoyl)propylcarbamoyl]-5-methyl-hexanohydroxamic acid

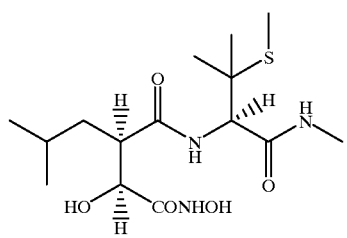

White solid. m.p. 150–151° C. $^1$H NMR; δ (CD$_3$OD), 4.38 (1H, s), 4.05 (1H, d, J=5.3 Hz), 2.77 (1H, m), 2.70 (3H, s), 1.99 (3H, s), 1.58 (2H, m), 1.33 (3H, s), 1.29 (4H, s and m), 0.89 (3H, d, J=7.6 Hz) and 0.86 (3H, d, J=6.6 Hz). $^{13}$C NMR; δ (CD$_3$OD), 175.4, 172.2, 171.5, 72.8, 60.0, 50.1, 47.1, 39.8, 26.9, 26.3, 26.2, 25.7, 23.6, 22.4 and 11.5.

EXAMPLE 8

2S-Hydroxy-3R-[1RS-(methylcarbamoyl)-2-trifluoromethyl-3,3,3-trifluoropropylcarbamoyl]-5-methyl-hexanohydroxamic acid

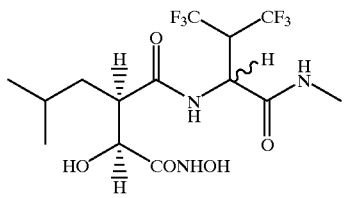

Mixture of diastereoisomers (3:1, SRS:SRR)

Off-white solid. m.p. 175–176° C. $^1$H NMR; δ (CD$_3$OD), 5.37 (0.66H, br m), 5.23 (0.33H, br m), 4.48 (1H, m), 4.12 (0.33H, d, J=9.2 Hz), 3.92 (0.66H, d, J=8.9 Hz), 2.99 (0.66H, m), 2.79 (0.66H, s), 2.72 (0.33H, s), 2.52 (0.33H, m), 1.74–1.38 (3H, br m) and 0.86 (6H, m). $^{13}$C NMR; δ (CD$_3$OD), 176.8, 176.6, 175.8, 171.7, 171.5, 171.0, 169.8, 169.4, 74.0, 73, 70.8, 41.0, 39.5, 37.8, 27.0, 26.8, 26.2, 25.9, 24.4, 24.0, 23.2, 22.1 and 21.5. Found: C 39.42, H 4.93, N 9.76%; C$_{14}$H$_{21}$F$_6$N$_3$O$_5$ requires C 39.54, H 4.98, N 9.88%.

EXAMPLE 9

3R-[2,2-Diphenyl-1S-(methylcarbamoyl)ethylcarbamoyl]-2S-hydroxy-5-methylhexanohydroxamic acid

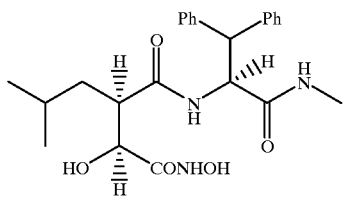

White solid. m.p. 201° C. (dec.). $^1$ H NMR; δ (CD$_3$OD), 7.22 (10H, m), 5.17 (1H, d, J=10.1 Hz), 4.48 (1H, d, J=10.0 Hz), 3.95 (1H, d, J=4.5 Hz), 2.58 (1H, m), 2.45 (3H, s), 1.32–1.05 (3H, br m), 0.78 (3H, d, J=6.0 Hz) and 0.67 (3H, d, J=6.0 Hz). $^{13}$C NMR; δ (CD$_3$OD), 175.2, 173.4, 171.4, 142.5, 141.9, 129.7, 129.6, 129.5, 129.4, 127.9, 72.4, 56.1, 54.3, 40.0, 26.4, 26.2, 23.4 and 22.1.

EXAMPLE 10

3R-[2-Benzylsulphanyl-2-methyl-1S-(methylcarbamoyl)propylcarbamoyl]-2S-hydroxy-6-phenyl-hexanohydroxamic acid

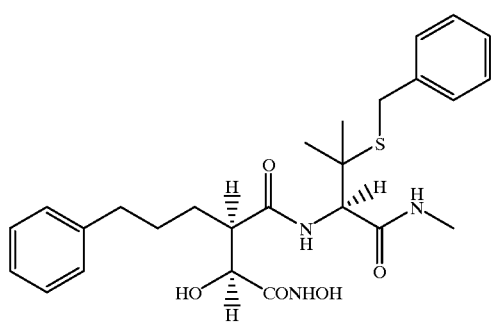

White solid. m.p. 155–156° C. $^1$H NMR; δ (CD$_3$OD), 7.30–7.04 (10H, m), 4.53 (1H, s), 4.10 (1H, d, J=5.6 Hz), 3.77 (2H, s), 2.75 (1H, m), 2.68 (3H, m) 2.59–2.49 (2H, m), 1.74–1.53 (4H, m), 1.38 (3H, s) and 1.34 (3H, s). $^{13}$C NMR; δ (CD$_3$OD), 175.4, 172.2, 171.5, 143.3, 139.1, 130.3, 129.5, 129.3, 127.9, 126.8, 72.7, 60.5, 51.4, 49.1, 36.7, 34.1, 30.6, 30.3, 26.8, 26.4 and 26.2. Found: C 59.52, H 6.83, N 8.17%; C$_{26}$H$_{35}$N$_3$O$_5$S.1.3 H$_2$O requires C 59.48, H 7.22, N 8.00%.

EXAMPLE 11

3R-[2-Cyclohexylmethylsulphanyl-2-methyl-1S-(methylcarbamoyl)propylcarbamoyl]-5-methyl-2S-hydroxy-hexanohydroxamic acid

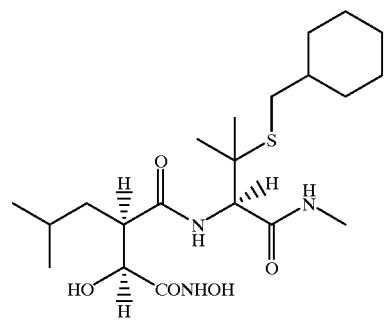

White solid. m.p. 166.5–168° C. $^1$H-NMR; δ (CD$_3$OD), 4.28 (1H, S), 3.99 (1H, d, J=5.0 Hz), 2.70 (1H, m), 2.63 (3H, s), 2.32 (2H, m), 1.74–1.45 (8H, br m), 1.27 (3H, s), 1.23 (9H, s and m) and 0.82 (6H, m). $^{13}$C-NMR; δ (CD$_3$OD), 175.2, 172.3, 171.4, 72.6, 60.6, 39.8, 39.4, 36.1, 34.1, 34.0, 27.4, 27.2, 26.8, 26.7, 26.5, 26.3, 23.6 and 22.4. IR (KBr disc); ν$_{max}$, 3233, 2925, 2851, 1652, 1585, 1523 and 1448 cm$^{-1}$. Found: C 53.03, H 8.85, N 9.07%; C$_{21}$H$_{39}$N$_3$O$_5$S.1.7 H$_2$O requires C 52.96, H 8.97, N 8.82%.

EXAMPLE 12

2S-Hydroxy-3R-[2-hydroxy-1RS-(methylcarbamoyl)-2-methyl-propylcarbamoyl]-5-methyl-hexanohydroxamic acid

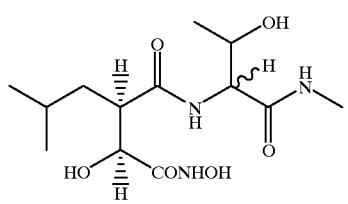

Mixture of diastereoisomers (5:3, SRS: SRR).

White foam. $^1$H-NMR; δ (CH$_3$OD), 4.22 (0.63H, s), 4.21 (0.37H, s), 3.86 (0.37H, d, J=6.1 Hz), 3.93 (0.63H, d, J=7.7 Hz), 2.84–2.71 (1H, m), 2.63 (3H, d, J=7.0 Hz), 1.63–1.36 (2H, m), 1.24–0.99 (7H, m) and 0.84–0.78 (6H, m). $^{13}$C-NMR; δ (CH$_3$OD), 176.0, 175.6, 173.5, 173.0, 171.6, 171.3, 73.6, 73.0, 72.6, 72.5, 61.9, 61.7, 39.5, 38.4, 27.6, 27.5, 27.1, 26.9, 26.4, 26.2, 23.8, 23.6, 22.3 and 22.0. IR (KBr disc); ν$_{max}$, 3319, 2959, 1651, 1532 and 1384 cm$^{-1}$. Found: C 47.53, H 8.02, N 12.12%; C$_{14}$H$_{27}$N$_3$O$_6$.1.1 H$_2$O requires C 47.61, H 8.33, N 11.90%.

EXAMPLE 13

2S-Hydroxy-3R-[2,2-diethyl-1S-(methylcarbamoyl)-butylcarbamoyl-5-methyl-hexanohydroxamic acid and 2S-Hydroxy-3R-[2,2-diethyl-1R-(methylcarbamoyl)-butylcarbamoyl]-5-methyl-hexanohydroxamic acid

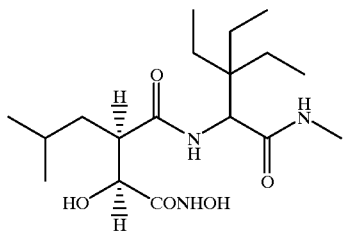

Diastereoisomers were separated following Step I and converted individually to the title compounds.

SRS Diastereoisomer:

Solid. m.p. 104–104.5° C. $^1$H-NMR; δ (CH$_3$OD), 7.91 (1H, d, J=4.6 Hz), 7.71 (1H, d, J=9.3 Hz), 7.21 (1H, m), 3.98 (1H, d, J=4.4 Hz), 2.70–2.61 (4H, m), 1.61–1.21 (9H, m) and 0.86–0.72 (15H, m). $^{13}$C-NMR; δ (CH$_3$OD), 175.3, 175.2, 174.0, 173.9, 171.5, 72.5, 58.8, 49.7, 42.8, 40.5, 27.5, 26.8, 26.5, 26.4, 23.5, 22.4 and 8.6. IR (KBr disc); $v_{max}$. 3270, 2964, 1649, 1523 and 1463 cm$^{-1}$. Found: C 55.06, H, 9.40, N 10.71%; C$_{18}$H$_{35}$N$_3$O$_5$.1.1 H$_2$O requires C 54.97, H 9.53, N 10.68%.

SRR Diastereoisomer:

Solid. m.p. 203–203.5° C. $^1$H-NMR; δ (CH$_3$OD), 7.73 (1H, d, J=8.9 Hz), 7.67 (1H, d, J=4.2 Hz), 4.20 (1H, m, J=5.0, 3.9 Hz), 3.84 (1H, d, J=8.2 Hz), 2.89–2.80 (1H, m), 2.55 (3H, m), 1.62–1.47 (1H, m), 1.38 (7H, t, J=7.6, 7.3 Hz), 1.03–0.89 (1H, m) and 0.83–0.69 (15H, m). $^{13}$C-NMR; δ (CH$_3$OD), 175.8, 174.2, 171.3, 73.8, 59.1, 42.7, 38.2, 27.6, 27.1, 26.3, 24.0, 21.9 and 8.6. IR (KBr disc) $v_{max}$, 3319, 2954, 1649 and 1531 cm$^{-1}$.

EXAMPLE 14

2S-Hydroxy-3R-[1RS-methylcarbamoyl-2-methyl-2-phenylpropylcarbamoyl]-5-methyl-hexanohydroxamic acid

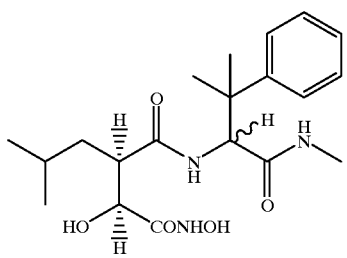

Mixture of diastereoisomers (1:1, SRS:SRR)

Solid. m.p. 130° C. $^1$H-NMR; δ (CH$_3$OD), 7.35–7.26 (2H, m), 7.25–7.13 (2H, m) 7.11–7.02 (1H, m), 4.64, 4.50 (1H, 2s), 3.92, 3.75 (1H, 2d, J=4.8, 8.0 Hz), 2.63–2.50 (1H, m), 2.52, 2.46 (3H, 2s), 1.37, 1.39, 1.32, 1.31 (6H, 4s), 1.30–1.10 (1H, m), 0.88–0.62 (2H, m) and 0.73. 0.68, 0.60. 0.49 (6H, 4d, J=6.3. 6.2, 5.9, 5.8 Hz). $^{13}$C-NMR; δ (CH$_3$OD), 175.5, 175.2, 173.0, 172.7, 171.5, 171.4, 147.8, 147.2, 129.3, 127.5, 127.3, 127.1, 73.5, 72.5, 62.6, 62.5, 42.4, 42.0, 39.9, 38.2, 28.3, 26.6, 26.1, 25.9, 25.3, 24.0, 23.5, 23.4, 175.5, 175.2, 173.0, 172.7, 171.5, 171.4, 147.8, and 21.9. IR (KBr disc); $v_{max}$, 3287, 3218, 2958, 1684, 1655, 1628, 1533 and 1072 cm$^{-1}$.

EXAMPLE 15

2S-Hydroxy-3R-[1S-tert-butylcarbamoyl-2-benzylsulphanyl-2-methyl-propylcarbamoyl]-5-methyl-hexanohydroxamic acid

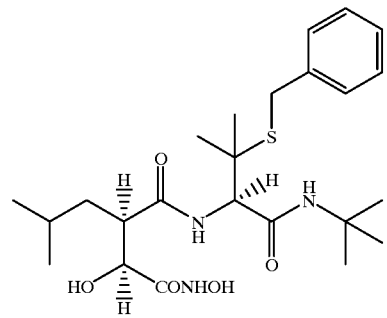

Solid. m.p. 76° C. (dec.). $^1$H-NMR; δ (CDCl$_3$), 9.51 (1H, br s), 8.42 (1H, br d, J=6.1 Hz), 7.40–7.17 (5H, m), 6.30 (1H, s), 4.56 (1H, d, J=7.8 Hz), 4.21 (1H, br, s), (2H, s), 3.50–3.38 (1H, m), 1.90–1.70 (1H, m), 1.70–1.40 (2H, m), 1.38 (3H, s), 1.29 (9H, s), 1.26 (3H, s), 0.92 (3H, d, J=5.4 Hz) and 0.90 (3H, d, J=5.8 Hz). $^{13}$C-NMR; δ (CDCl$_3$), 175.2, 168.3, 168.3. 137.9, 129.0, 128.7, 127.2, 73.1, 58.7, 52.0. 48.6, 44.2, 39.1, 33.3, 28.4, 26.1, 25.8, 25.0, 22.6 and 22.2. IR (KBr disc); $v_{max}$, 3314, 2962, 1646, 1534, 1455, 1389, 1367, 1222 and 1070 cm$^{-1}$.

EXAMPLE 16

2S-Hydroxy-3R-[1S-(methylcarbamoyl)-2-mercapto-2-methyl-propylcarbamoyl]-5-methyl-hexanohydroxamic acid

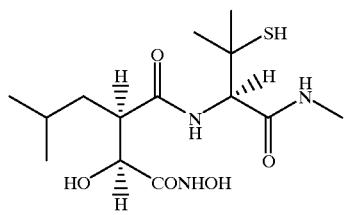

White solid. m.p. 158–160° C. $^1$H-NMR; δ (CD$_3$)$_2$SO), 10.43 (1H, s), 8.74 (1H, s), 7.64 (1H, d, J=4.5 Hz), 7.51 (1H, d, J=9.5 Hz), 5.31 (1H, d, J=7.5 Hz), 4.31 (1H, d, J=9.5 Hz), 3.60 (1H, t, J=7.9 Hz), 2.60 (1H, m), 2.42 (3H, d, J=4.3 Hz), 2.35 (1H, s), 1.35–1.1 (2H, m), 1.21(3K, s), 1.14 (3H, s), 0.80 (1H, m) and 0.64 (6H, m). $^{13}$C-NMR; δ (CD$_3$)$_2$SO), 172.4, 169.5, 168.7, 71.3, 60.7, 47.8, 46.0, 37.4, 32.8, 30.4, 28.5, 25.6, 25.4, 25.3, 23.4 and 21.8. IR (KBr disc); $v_{max}$, 3300, 2959, 2578, 1634, 1528, 1467, 1408, 1369, 1307, 1144, 1067 cm$^{-1}$. Found: C 47.96, H 7.71, N 11.51%; C$_{14}$H$_{27}$N$_3$O$_5$S.0.2 H$_2$O requires C 47.63, H 7.82, N 11.90%.

EXAMPLE 17

2S-Hydroxy-3R-[S-(methylcarbamoyl)-adamant-1-ylmethylcarbamoyl]-5-methyl-hexanohydroxamic acid and 2S-Hydroxy-3R-(S-methylcarbamoyl-adamant-1-ylmethylcarbamoyl)-5-methyl-hexanohydroxamic acid

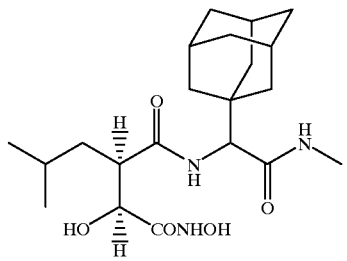

Diastereoisomers were separated following Step I and converted individually to the title compounds.

Diastereoisomer A:

Solid. m.p. 134° C. $^1$H-NMR; δ (CD$_3$)$_2$SO), 8.70 (1H, br s), 7.66–7.48 (2H, m), 5.25 (1H, br s), 3.79 (1H, d, J=8.5 Hz), 3.62–3.50 (1H, m), 2.78–2.61 (1H, m), 2.38 (3H, d, J=3.5 Hz), 1.84–1.61 (3H, m), 1.60–1.20 (15H, m), 0.69 (3H, d, J=5.9 Hz) and 0.66 (3H, d, J=6.2 Hz). $^{13}$C-NMR; δ (CD$_3$)$_2$SO), 172.9, 169.9, 168.5, 71.6, 61.2, 47.2, 38.3, 37.0, 36.4, 35.4, 27.8, 25.4, 25.2, 23.6 and 21.5. IR (KBr disc); $v_{max}$, 3298, 2904, 1655, 1626 and 1540 cm$^{-1}$.

Diastereoisomer B:

Solid. m.p. 200° C. $^1$H-NMR; δ ((CD$_3$)$_2$SO/CD$_3$OD), 7.64 (1H, d, J=4.5 Hz), 7.26 (1H, d, J=9.0 Hz), 3.85 (1H, d), 3.59 (1H, d, J=7.9 Hz), 2.60–2.45 (1H, m), 2.41 (3H, d, J=4.2 Hz), 1.80–1.65 (3H, m), 1.58–1.19 (15H, m), 0.65 (3H, d, J=6.4 Hz) and 0.62 (3H, d, J=6.4 Hz). $^1$H-NMR; δ ((CD$_3$)$_2$SO/CH$_3$OD), 172.6, 170.2, 169.2, 71.5, 61.3, 37.8, 36.7, 35.9, 28.1, 25.5, 25.3, 25.2, 23.4 and 21.9. IR (KBr disc); $v_{max}$, 3292, 2907, 2850, 1646, 1628, 1509 cm$^{-1}$.

EXAMPLE 18

2S-Hydroxy-3R-[2-methoxy-1RS-(methylcarbamoyl)-2-methyl-propylcarbamoyl]-5-methyl-hexanohydroxamic acid

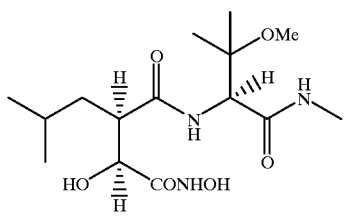

3.5: 5 mixture of diastereoisomers

Foam. $^1$H-NMR; δ (CH$_3$OD, partial exchange),7.93 (0.25H, d, J=8.0 Hz), 7.82 (0.25H, d, J=8.7 Hz), 7.69–7.55 (0.5H, m), 4.32–4.24 (1H, m), 3.96 (0.4H, d, J=5.8 Hz), 3.87 (0.6H, d, J=7.6 Hz), 3.11 (3H, d, J=5.8 Hz), 2.87–2.69 (1H, m), 2.64–2.59 (3H, m), 1.61–1.37 (2H, m), 1.20–0.99 (7H, m) and 0.81 (6H, dd, J=7.2, 7.0 Hz). $^{13}$C-NMR: δ (CH$_3$OD), 175.9, 175.6, 172.6, 172.5, 171.5, 171.4, 77.4, 76.8, 73.6, 73.0, 61.7, 61.2, 49.9, 39.6, 38.5, 27.1, 26.9, 26.3, 23.9, 23.6, 22.9, 22.7, 22.4, 22.0 and 21.9. IR (KBr disc); $v_{max}$, 3307, 2943, 1649, 1531, 1467, 1408, 1384, 1361, 1067 cm$^{-1}$.

EXAMPLE 19

2S-Hydroxy-3R-(2-methoxycarbonyl-1RS(-methylcarbamoyl)-2-methyl-propylcarbamoyl]-5-methyl-hexanohydroxamic acid

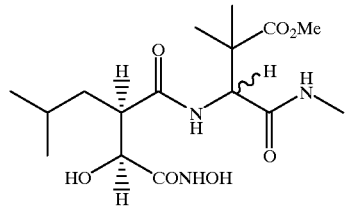

Mixture of diastereoisomers.

White foam. $^1$H-NMR; δ ((CD$_3$)$_2$SO, major diastereoisomer), 10.62 (1H, s), 8.99 (1H, s), 8.37 (1H, d, J=10.0 Hz), 7.58 (1H, d, J=4.0 Hz), 5.94 (1H, s), 4.95 (1H, m), 3.85 (1H, d, J=6.5 Hz), 3.56 (3H, s), 2.96 (1H, m), 2.58 (3H, m), 1.54–1.32 (3H, m), 0.91 (3H, s), 0.83 (3H, s) and 0.68 (6H, m). $^{13}$C-NMR; δ ((CD$_3$)$_2$SO, major diastereoisomer), 175.8, 173.9, 169.6, 167.9, 72.1, 57.3, 51.5, 46.9, 43.4, 36.2, 25.6, 25.1, 23.8, 23.2 and 18.7. IR (KBr disc); $v_{max}$, 3376, 2956, 1717, 1653, 1540, 1448, 1269 and 1143 cm$^{-1}$.

EXAMPLE 20

3R-[2-Methylthio-2-methyl-1S-(methylcarbamoyl) propylcarbamoyl]-5-methyl-2S-propen-2-yl-hexanohydroxamic acid

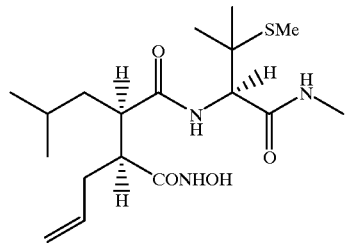

STEP A:

3R,S-Allyl-2R-isobutyl-butan-1,4-dioic acid-4-tert-butyl ester (1:9, RS:RR)

To a stirred solution of 2R-isobutyl-butan-1,4-dioic acid-4-tert-butyl ester (5 g, 21.7 mmol) in dry THF (100 ml), under an argon atmosphere, at −78° C., was added 1.5M LDA (31.8 ml, 47.7 mmol) dropwise via cannula. After stirring the solution at −78° C. for 1 hour, allyl bromide (2.44 ml, 28.2 mmol) was added dropwise via syringe. The resulting solution was allowed to warm to room temperature over a 2 hour period. Methanol (10 ml) was added and the solution stirred at room temperature. After 30 minutes the reaction mixture was concentrated under reduced pressure. The residue was taken up in dichloromethane (100 ml) and washed with 1M hydrochloric acid (100 ml) and brine (100 ml). The dichloromethane layer was dried over anhydrous magnesium sulphate, filtered and solvent removed under reduced pressure to give the title compound as a golden oil (5.6 g, 97%) (1:9, RS:RR) $^1$H-NMR; δ (CDCl$_3$, major diastereoisomer), 5.78–5.63 (1H, m), 5.01–5.11 (2H, m), 2.57–2.72 (2H, m), 2.37 (2H, m), 1.52–1.67 (2H, m), 1.42 (9H, s), 1.37 (1H, m) and 0.90 (6H, d, J=6.3 Hz). $^{13}$C-NMR; δ (CDCl$_3$. major diastereoisomer) 181.1, 172.9, 134.6, 117.3, 81.2, 47.8, 44.3, 38.4, 27.9, 25.9, 23.5, and 21.5.

STEP B:
3S-Allyl-2R-isobutyl-butan-1,4-dioic acid-4-tert-butyl ester (dicyclohexylamine salt)

(i) To a stirred solution of 3R,S-allyl-2R-isobutyl-butan-1,4-dioic acid-4-tert-butyl ester (1:9, RS:RR) (5.11 g, 18.9 mmol) in dry THF (100 ml) under argon at −78° C. was added 1.5M LDA (27.7 ml, 41.6 mmol) via cannula. The reaction mixture was warmed to room temperature over a 2 hour period then cooled back to −78° C. and methanol (8 ml) was added via syringe. The reaction was then allowed to warm to room temperature for a further 2 hours. The solvent was removed under reduced pressure. The residue was taken up in dichloromethane (150 ml) and washed with 1M hydrochloric acid (150 ml) and brine (150 ml). The dichloromethane layer was dried over anhydrous magnesium sulphate, filtered and the solvent removed under reduced pressure to yield the title compound (3:2, RS:RR), as a brown oil (4.7 g, 92%).

(ii) Utilising the epimerisation procedure described in Step B(i). but employing a reaction temperature of −78° C. after addition of LDA in lieu of allowing the reaction mixture to warm to room temperature yielded the title compound, as the major diastereomer as a brown oil (4.6 g, 98%) (3:1, RS:RR). $^1$H-NMR; δ (CDCl$_3$, major diastereoisomer), 11.60 (1H, br s), 5.75–5.61 (1H, br m), 5.06–4.96 (2H, br m), 2.70–2.52 (2H, br m), 2.36–2.19 (2H, br m), 1.65–1.44 (2H, br m), 1.40 (9H, s), 1.13 (1H, m) and 0.86 (6H, dd, J=4.4, 2.1 Hz). $^{13}$C-NMR; δ (CDCl$_3$, major diastereoisomer) 180.7, 172.2, 134.6, 117.1, 81.0, 48.6, 45.7, 38.9, 34.8, 33.4, 27.9, 26.2 and 21.2.

(iii) The above reaction was repeated and the combined products (36.85 g, 136 mmol) were dissolved in hexane and the solution allowed to stand overnight before filtering through glass microfibre filter papers (Whatman GFF) to remove a small amount of a coloured solid. Dicyclohexylamine (27 ml, 136 mmol) was added to the filtrate: crystallisation commenced after approximately 30 minutes. The mixture was chilled in a refridgerator overnight and the product was collected by filtration, washed with cold hexane and dried under vacuum. Yield: 14.19 g (23%). $^1$H-NMR δ (CDCl$_3$), 6.89–6.58 (2H, m), 5.76 (1H, m), 5.08–4.91 (2H, m), 2.99–2.82 (2H, m), 2.53–2.26 (4H, m), 2.09–1.93 (4H, m), 1.86–1.56 (8H, m), 1.54–0.99 (11H, m), 1.42 (9H, s), 0.92 (3H, d, J=6.5 Hz). 0.87 (3H, d, J=6.5 Hz). $^{13}$C-NMR; δ (CDCl$_3$, single diastereoisomer), 179.0, 173.9, 135.9, 115.7, 79.7, 52.1, 50.8, 49.7, 41.2, 35.9, 29.2, 29.1, 27.9, 26.5, 25.1, 24.6, 24.0 and 21.5.

STEP C:
3R-[2-Methyllthio-2-methyl-1S-(methylcarbamoyl) propylcarbamoyl]-5-methyl-2S-propen-2-yl-hexanoic acid tert-butyl ester To a cooled 0° C. solution of S-methyl-L-penicillamine-N-methylamide (1.60 g, 9.1 mmol) and 3S-allyl-2R-isobutyl-butan-1,4-dioic acid-4-tert-butyl ester DCHA salt (4.5 g, 10.0 mmol) in ethyl acetate (130 ml) was added HOBt (1.47 g, 10.9 mmol) and EDC (2.09 g, 10.9 mmol). The mixture was heated at reflux for 4 hours then stirred overnight at room temperature. The solid precipitate was removed by filtration and the filtrate was washed with 1M hydrochloric acid. 0.5M sodium carbonate and brine, dried over anhydrous magnesium sulphate, filtered and the solvent removed under reduced pressure. The residue was purified by column chromatography (silica gel, 5% methanol in dichloromethane) to afford a yellow foam (3.0 g, 77%) which was used without further purification. $^1$H-NMR; δ (CDCl$_3$), 6.77 (1H, m), 6.67 (1H, d, J=8.4 Hz), 5.70 (1H, m), 5.00 (2H, ddd, J=16.8, 7.6, 1.7 Hz), 4.53 (1H, d, J=8.4 Hz), 2.79 (3H, d, J=4.8 Hz), 2.52 (2H, m), 2.26 (2H, m), 2.08 (3H, s), 1.65 (1H, m), 1.46 (1H, m), 1.43 (9H, s), 1.38 (3H, s), 1.29 (3H, s), 1.12 (1H, m), 0.88 (3H, d, J=6.4 Hz) and 0.85 (3H, d, J=6.4 Hz)

STEP D:
3R-[2-Methyllthio-2-methyl-1S-(methylcarbamoyl) propylcarbamoyl]-5-methyl-2S-propen-2-yl-hexanoic acid 3R-[2-Methyllthio-2-methyl-1S-(methylcarbamoyl) propylcarbamoyl]-5-methyl-2S-propen-2-yl-hexanoic acid tert-butyl ester (3.0 g, 7.0 mmol) was dissolved in dichloromethane (80 ml) and TFA (80 ml) and the solution was stored at 0° C. overnight. The solvents were removed under reduced pressure and the residue was azeotroped with toluene to leave a yellow foam (3.07 g, contained residual TFA) which was used without further purification.

STEP E:
3R-[2-Methyllthio-2-methyl-1S-(methylcarbamoyl) propylcarbamoyl]-5-methyl-2S-propen-2-yl-hexanohydroxamic acid.

3R-[2-Methyllthio-2-methyl-1S-(methylcarbamoyl) propylcarbamoyl]-5-methyl-2S-propen-2-yl-hexanoic acid was dissolved in DMF (40 ml) and cooled to 0° C. before successive addition of HOBt (1.14 g, 8.4 mmol), NMM (450 μl) and EDC (1.61 g, 8.4 mmol). The reaction mixture was allowed to cool to room temperature and stirred for two hours, cooled to 0° C. and treated with hydroxylamine hydrochloride (731 mg, 10.5 mmol) and NMM (1.16 ml, 10.5 mmol). The reaction mixture was stirred overnight at room temperature. The solvent was removed under reduced pressure and the residue was triturated with water (40 ml) and diethyl ether (40 ml). The white solid which precipitated was collected by filtration, washed successively with diethyl ether and ethyl acetate and dried at 80° C. under high vacuum. Yield: 1.49 g (53%). m.p. 227.5° C. $^1$H-NMR; δ ((CD$_3$)$_2$SO), 10.29 (1H, s), 8.61 (1H, s), 7.90 (2H, m), 5.43 (1H, m), 4.71 (2H, m), 4.37 (1H, d, J=9.4 Hz), 2.52 (1H, m), d, J=4.5 Hz), 2.09 (3H, m), 1.85 (3H, s), 1.24 (2H, m), 1.15 (3H, s), 1.11 (3H, s), 0.79 (1H, m), 0.63 (3H, d, J=6.4 Hz) and 0.58 (3H, d, J=6.4 Hz). $^{13}$C-NMR; δ ((CD$_3$)$_2$SO), 172.3, 168.2, 168.1, 134.9, 114.6, 55.8, 44.9, 44.7, 44.6, 33.5, 24.2, 24.1, 22.9, 22.7, 20.4 and 9.5. Found: C 55.17, H 8.57, N 10.81%; C$_{18}$H$_{33}$N$_3$O$_4$S.0.2 H$_2$O requires C 55.27, H 8.61, N 10.74%.

The following additional compounds were prepared as single diastereoisomers (unless otherwise stated) by methods of Example 20, starting from the appropriate amino acids:

EXAMPLE 21

3R-[2-Cyclohexylmethylsulphanyl-2-methyl-1S-(methylcarbamoyl)propyl-carbamoyl]-5-methyl-2S-propen-2-yl-hexanohydroxamic acid

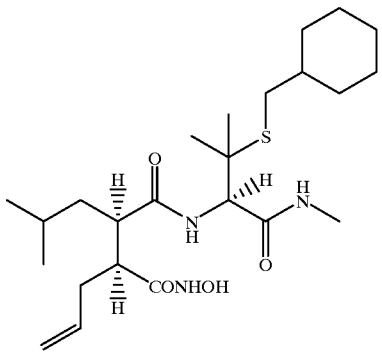

White solid. m.p. 187–188.5° C. $^1$H-NMR; δ (CH$_3$OD), 5.58 (1H, m), 4.88 (2H, m), 4.40 (1H, s), 2.60 (3H, s), 2.57 (1H, m), 2.38 (2H, m), 2.23 (3H, m), 1.72–1.51 (4H, br m), 1.28 (3H, s), 1.26 (3H, s), 1.17 (4H, m), 1.11–0.86 (6H, br m), 0.76 (3H, d, J=6.4 Hz) and 0.72 (3H, d, J=6.5 Hz). $^{13}$C-NMR; δ (CH$_3$OD), 176.3, 172.4, 172.0, 136.4, 117.2, 59.7, 41.6, 39.3, 36.3, 36.1, 34.3, 34.2, 27.4, 27.2, 27.0, 26.9, 26.2, 26.0, 24.9, 24.3 and 21.9 Found: C 59.94, H 9.15, N 8.84%; C$_{24}$H$_{43}$N$_3$O$_4$S.0.6 H$_2$O requires C 59.99, H 9.27, N 8.75%.

EXAMPLE 22

3R-[2-Benzylsulphanyl-2-methyl-1S-(methylcarbamoyl)-propylcarbamoyl]-5-methyl-2S-propen-2-yl-hexanohydroxamic acid

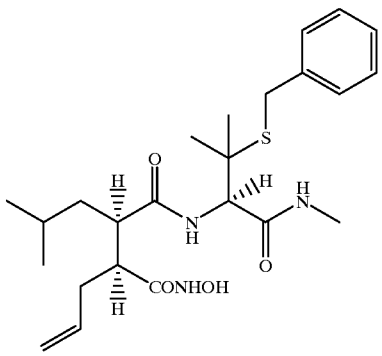

White solid. m.p. 212–213° C. $^1$H-NMR; δ (CH$_3$OD), 7.26 (5H, m), 5.56 (1H, m), 4.86 (2H, m), 4.75 (1H, s), 3.91 (1H, d, J=10.8 Hz), 3.76 (1H, d, J=10.9 Hz), 2.69 (3H, s), 2.65 (1H, m), 2.49 (1H, m), 2.23 (2H, m), 1.53 (2H, m), 1.44 (3H, s), 1.35 (3H, s), 1.12 (1H, m), 0.84 (3H, d, J=6.5 Hz) and 0.80 (3H, d, J=6.5 Hz). $^{13}$C-NMR; δ (CD$_3$)$_2$SO), 173.6, 169.5, 137.9, 136.1, 129.0, 128.2, 126.5, 115.7, 58.0, 48.3, 46.4, 46.1, 34.7, 32.5, 26.3, 25.4, 25.3, 24.6, 23.7 and 21.8.

EXAMPLE 23

3R-[2,2-Diphenyl-1S-(methylcarbamoyl)-propylcarbamoyl]-5-methyl-2S-propen-2-yl-hexanohydroxamic acid

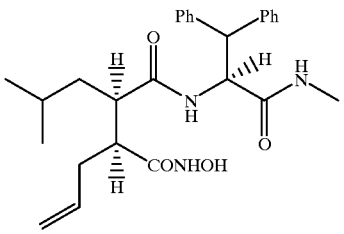

White solid. m.p. 243° C. (dec.). $^1$H NMR; δ (CD$_3$)$_2$SO), 10.33 (1H, s), 8.68 (1H, s), 8.36 (1H, d, J=8.9 Hz), 7.78 (1H, d, J=4.7 Hz), 7.40–7.04 (10H, br m), 5.27 (2H, m), 4.76 (1H, d, J=9.5 Hz), 4.64 (1H, d, J=17.0 Hz), 4.36 (1H, d, J=11.6 Hz), 3.32 (1H, m), 2.29 (3H, d, J=3.9 Hz), 2.22 (1H, m), 1.95 (1H, m), 1.46 (1H, m), 1.26 (2H, br m), 0.94 (1H, br m) and 0.75 (6H, m). $^{13}$C NMR; δ ((CD$_3$)$_2$SO), 172.9, 170.3, 169.3, 141.8, 135.9, 128.3, 128.0, 127.9, 126.2, 115.4, 55.6, 52.6, 46.3, 45.7, 33.7, 25.2, 23.8 and 21.6. Found: C 67.70, H 7.62, N 9.11%; C$_{27}$H$_{35}$N$_3$O$_4$.0.7 H$_2$O requires C 67.82, H 7.67, N 8.79%.

EXAMPLE 24

3R-[2-Mercapto-2-methyl-1S-(methylcarbamoyl)-propylcarbamoyl]-5-methyl-2S-propen-2-yl-hexanohydroxamic acid

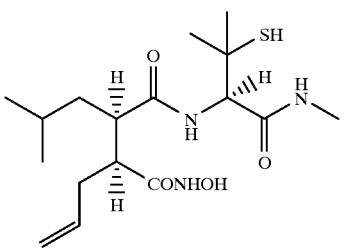

Off-white solid. m.p. 191–193° C. $^1$H-NMR; δ ((CD$_3$)$_2$SO), 10.31 (1H, s), 7.87 (1H, d, J=8.9 Hz), 7.77 (1H, d, J=4.7 Hz), 5.46 (1H, m), 4.72 (2H, m), 4.31 (1H, d, J=8.9 Hz), 2.61 (1H, s), 2.55 (1H, m), 2.40 (3H, d, J=3.9 Hz), 2.17–1.95 (3H, br m), 1.21 (6H, 2s), 1.03 (2H, m), 0.85 (1H, m), 0.65 (3H, d, J=6.2 Hz) and 0.59 (3H, d, J=6.4 Hz). $^{13}$C-NMR; δ ((CD$_3$)$_2$SO), 172.4, 167.9, 167.3, 134.6, 114.8, 59.8, 44.8, 44.6, 33.6, 28.4, 28.1, 24.2, 22.7, 20.4 and 20.0. IR (KBr disc); ν$_{max}$, 3282, 3077, 2957, 2932, 1629, 1546, 1467, 1412, 1387, 1369 and 1258 cm$^{-1}$. Found: C 53.94, H 8.25, N 10.65%; C$_{17}$H$_{31}$N$_3$O$_4$S.0.4 H$_2$O requires: C 53.63, H 8.42, N 11.04%.

EXAMPLE 25

3R-[2,2-diethyl-1RS-(methylcarbamoyl)-butylcarbamoyl]-5-methyl-2S-propen-2-yl-hexanohydroxamic acid

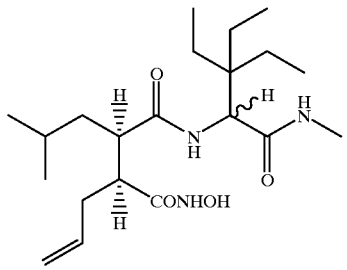

Mixture of diastereoisomers (ca. 7:1. SRS:SRR)

Solid. m.p. 227–228° C. $^1$H-NMR; δ (CD$_3$OD), 7.89 (0.13H, d, J=4.0 Hz), 7.81 (0.87H, J=4.5 Hz), 7.68 (1H, d, J=9.3 Hz), 5.64–5.47 (1H, m), 4.93–4.82 (2H, m) 4.32 (0.87H, d, J=9.3 Hz), 4.28 (0.13 H, d), 2.59–2.53 (4H, m), 2.22–1.99 (3H, m), 1.50–1.24 (8H, m), 1.03–0.92 (1H, m) and 0.82–0.70 (15H, m). $^{13}$C-NMR; δ (CH$_3$OD), 176.3, 173.6, 172.4, 136.4, 136.1, 117.5, 59.0, 48.0, 42.5, 41.9, 36.3, 27.4, 27.1, 26.3, 24.4, 22.0 and 8.7. IR (KBr disc); $v_{max}$, 3300, 2953, 1638, 1521, 1460 and 1381 cm$^{-1}$.

EXAMPLE 26

3R-[2-Benzylsulphanyl-2-methyl-1S-(methylcarbamoyl)-propylcarbamoyl]-5-methyl-2S-phthalimidomethyl-hexanohydroxamic acid

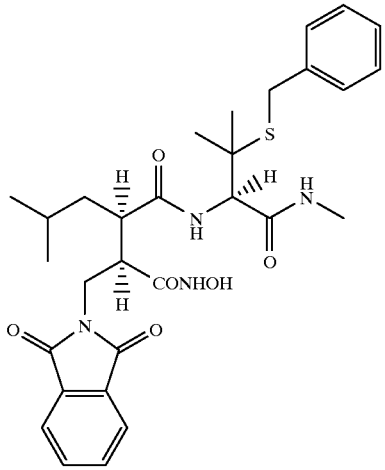

STEP A:
2-Benzyloxycarbonyl-3R-tert-butoxycarbonyl-5-methyl-2-phthalimidomethyl-hexanoic acid benzyl ester To an ice-cooled solution of 2-benzyloxycarbonyl-3R-tert-butoxycarbonyl-5-methylhexanoic acid benzyl ester (prepared by the method described in EP 0 446 267) (39.4 g, 86.78 mmol) in dry DMF (400 ml) was added sodium hydride (60% dispersion in mineral oil, 3.83 g, 95.46 mmol) with stirring. The reaction mixture was maintained at 0° C. for 20 mins then allowed to warm to room temperature and stirred for a further 2.5 h. After cooling to 0° C., N-(bromomethyl)phthalimide (25 g, 104.1 mmol) was added and the mixture was stirred for 0.5 h at 0° C. then at room temperature overnight. The solvent was removed under reduced pressure to leave an oil which was extracted with diethyl ether (400 ml) and the solid residues were removed by filtration. The filtrate was washed successively with water (300 ml), 1M hydrochloric acid (300 ml) and brine (300 ml), dried over anhydrous magnesium sulphate and filtered. The solution was concentrated in vacuo to leave a yellow oil which was purified by column chromatography (silica gel, 50% diethyl ether in hexane) to afford the title compound as a colourless oil (26.24 g, 49%). $^1$H-NMR; δ (CDCl$_3$), 7.78 (2H, m), 7.67 (2H, m), 5.28–5.05 (4H, br m), 4.54–4.35 (2H, br m), 3.03 (1H, m), 1.86 (1H, m), 1.68 (1H, m), 1.50 (9H, s), 1.49 (1H, m), 0.82 (3H, d, J=6.6 Hz) and 0.78 (3H, d, J=6.5 Hz).

STEP B:
3R-tert-Butoxycarbonyl-5-methyl-2-phthalimidomethyl-hexanoic acid

2-Benzyloxycarbonyl-3R-tert-butoxycarbonyl-5-methyl-2-phthalimidomethyl-hexanoic acid benzyl ester (26.24 g, 42.8 mmol) was deprotected by catalytic transfer hydrogenolysis in ethanol, according to the method described in Example 32 (Step B). The solvent was removed under reduced pressure the residue was dissolved in toluene (250 ml) and NMM (4.33 g, 42.8 mmol) was added. The mixture was heated under reflux for 2 h. Solvents were evaporated and the remaining oil was dissolved in ethyl acetate and the solution was washed with 5% citric acid (2×200 ml) and brine (200 ml), dried over anhydrous magnesium sulphate and filtered. The solvent was removed, leaving the desired product as a yellow foam (16.58 g, including residual solvent) which was used directly in Step C. $^1$H-NMR; δ (CDCl$_3$), 7.83 (2H, m), 7.72 (2H, m), 4.12 (1H, m), 3.83 (1H, m), 3.21 (1H, m), 2.72 (1H, m), 1.81–1.55 (2H, br m), 1.48 (9H, s), 1.31 (1H, m) and 0.92 (6H, m).

STEP C:
3R-tert-Butoxycarbonyl-5-methyl-2-phthalimidomethyl-hexanoic acid benzyl ester 3R-tert-Butoxycarbonyl-5-methyl-2-phthalimidomethyl-hexanoic acid (16.58 g, 42.56 mmol) was dissolved in dry DMF and placed under a blanket of argon. The solution was cooled in an ice bath, benzyl bromide (5.56 ml, 46.82 mmol) and anhydrous sodium carbonate (4.96 g, 46.82 mmol) were added and the mixture was left to stir overnight at room temperature. The solvent was removed under reduced pressure and the residual oil was dissolved in diethyl ether (300 ml) and washed successively with water (2×200 ml), 1M hydrochloric acid (2×200 ml) and brine (200 ml). The organic phase was dried (anhydrous magnesium sulphate), filtered and evaporated to a crude yellow oil which was purified by column chromatography (silica gel, gradient elution, 30→50% diethyl ether in hexane). The desired product was isolated as a pale yellow oil (18.2 g, 89%; 3:2 mixture of diastereoisomers). $^1$H-NMR; δ (CDCl$_3$), 7.78 (2H, m), 7.67 (2H, m), 7.24 (5H, m), 5.05 (2H, m), 4.97 (1H, d, J=8.2 Hz), 4.18–4.04 (1H, br m), 3.81 (1H, br m), 3.15 (1H, m), 2.73 (1H, m), 1.72–1.53 (2H, br m), 1.50 (5.4H, s), 1.41 (3.6H, s), 1.11 (1H, m) and 0.90 (6H, m).

STEP D:
3R-Carboxy-5-methyl-2-phthalimidomethyl-hexanoic acid benzyl ester 3R-tert-Butoxycarbonyl-5-methyl-2-phthalimidomethyl-hexanoic acid benzyl ester was deprotected by acidolysis with TFA according to the procedure described in Example 1 (Step G). The product was isolated as a pale yellow oil (16.54 g, including residual solvent) and was used in Step E without further purification. $^1$H-NMR; δ (CDCl$_3$, 3:2 mixture of diastereoisomers), 8.28 (1H, br s), 7.78 (2H, m), 7.68 (2H, m), 7.25 (5H, m), 5.08 (2H, m), 4.15 (1H, m), 3.89 (1H, m), 3.25 (1H, m), 2.88 (1H, m), 1.82–1.52 (2H, br m), 1.25 (1H, m), and 0.89 (6H, m).

STEP E:
3R-[2-Benzylsulphanyl-2-methyl-1S-(methylcarbamoyl) propylcarbamoyl]-5-methyl-2RS-phthalimidomethylhexanoic acid benzyl ester 3R-Carboxy-5-methyl-2-phthalimidomethyl-hexanoic acid benzyl ester (8.61 g, 20.33 mmol) was dissolved in dry DMF (100 ml) and the solution was cooled in an ice bath while HOBt (3.30 g, 24.40 mmol) and EDC (4.68 g, 24.40 mmol) were added. The reaction mixture was stirred at 0° C. for 0.5 h then at room temperature for 2 h to ensure complete formation of the activated ester. A solution of S-benzyl-L-penicillamine-N-methylamide (6.67 g, 26.43 mmol) in dry DMF (20 ml) was added. The reaction mixture stirred at room temperature for 3 days. The solvent was evaporated under reduced pressure, the residue was dissolved in diethyl ether (250 ml) and the solution was washed successively with 5% aq. sodium hydrogen carbonate (2×100 ml), 5% citric acid (2×100 ml) and brine. The organic phase was dried (anhydrous magnesium sulphate), filtered and evaporated under reduced pressure to leave a yellow foam. Column chromatography (silica gel, gradient elution, 50→100% diethyl ether in hexane) gave the desired product as an inseparable 3:1 mixture of diastereoisomers (9.26 g. 69%). $^1$H-NMR: δ (CDCl$_3$, partial exchange), 8.32 (0.5H, m), 8.12 (0.5H, m), 7.78–7.62 (4H, br m), 7.27–6.89 (5H, br m), 4.66 (1H, m), 4.04–3.67 (4H, br m), 3.02 (1H, m), 2.80 (1H, m), 2.66 (3H, m), 1.62 (1H, m), 1.38 (2.25H, s), 1.35 (0.75H, s), 1.32 (2.25H, s), 1.30 (0.75H, s), 1.38 (1H, m), 1.14 (1H, m) and 0.77 (6H, br m).

STEP F:
3R-[2-Benzylsulphanyl-2-methyl-1S-(methylcarbamoyl) propylcarbamoyl]-5-methyl-2RS-phthalimidomethylhexanoic acid 3R-[2-Benzylsulphanyl-2-methyl-1S-(methylcarbamoyl) propylcarbamoyl]-5-methyl-2RS-phthalimidomethylhexanoic acid benzyl ester (8.18 g, 12.43 mmol) was dissolved in 30% HBr in glacial acetic acid (50 ml) and stirred at 50° C. for 15 min. The solvent was evaporated under reduced pressure leaving an oil, which was azeotroped twice with toluene. The residue was dissolved in ethyl acetate (200 ml) and the solution was washed with water, dried over anhydrous magnesium sulphate, filtered and evaporated. The product was further purified by column chromatography (silica gel, gradient elution, 0→10% dichloromethane in methanol), to afford the title compound as a 3:2 mixture of diastereoisomers (2.27 g, 32%). $^1$H-NMR, δ (CH$_3$OD), 7.78 (2H, m), 7.71 (2H, m), 7.40–7.18 (10H, br m), 7.14 (1H, m), 6.40 (1H, m), 5.03 (2H, m), 4.62 (0.6H, d, J=8.4 Hz), 4.52 (0.4H, d, J==8.3 Hz), 4.07 (1H, m), 3.94–3.78 (2H, m), 3.18 (1H, m), 2.80 (3H, m), 2.72 (1H, m), 1.88–1.61 (2H, br m), 1.53 (1.8H, s), 1.48 (1.2H, s), 1.40 (1.8H, s), 1.36 (1.2H, s), 1.17 (1H, m) and 0.95–0.75 (6H, m).

STEP G:
3R-[2-Benzylsulphanyl-2-methyl-1S-(methylcarbamoyl)-propylcarbamoyl]-5-methyl-2S-phthalimidomethyl-hexanohydroxamic acid 3R-[2-Benzylsulphanyl-2-methyl-1S-(methylcarbamoyl)-propylcarbamoyl]-5-methyl-2RS-phthalimidomethylhexanoic acid was converted to the corresponding hydroxamic acid by the method described in Example 20 (Step E). The solvent was removed under reduced pressure and the residue was triturated with diethyl ether and water to give a white precipitate which collected by filtration. The precipitate was slurried in hot ethyl acetate and the mixture was cooled and filtered. The desired product was obtained as a white solid which was dried under high vaccum (1.27 g, 48%). m.p. 199–201° C. $^1$H-NMR; δ (CH$_3$OD), 7.68 (4H, m), 7.18 (2H, m), 7.02 (2H, m), 6.91 (1H, m), 4.70 (1H, s), 3.99 (1H, m), 3.85 (1H, m), 3.71 (2H, m), 2.91–2.71 (2H, br m), 2.64 (3H, s), 1.53 (1H, m), 1.39 (3H, s), 1.35 (3H, s), 1.31 (3H, s), 1.02 (1H, m), 0.80 (3H, d, J=6.5 Hz) and 0.74 (3H, d, J=6.6 Hz). $^{13}$C-NMR; δ (CH$_3$OD), 175.8, 175.7, 172.1, 172.0, 170.1, 169.1, 162.8, 162.0, 161.2, 139.0, 135.3, 133.3, 130.3, 129.3, 127.7, 124.2, 59.8, 59.7, 49.4, 46.6, 46.3, 46.3, 41.5, 39.6, 34.0, 27.4, 27.1, 26.4, 26.2, 24.6, 24.3 and 21.9. IR (KBr disc) $v_{max}$, 3334, 2956, 2365, 1773, 1718, 1645, 1522, 1467, 1431 and 1394 cm$^{-1}$. Found: C 60.09, H 6.68 N 9.64%; C$_{30}$H$_{38}$N$_4$O$_6$S.0.9 H$_2$O requires: C 60.16, H 6.70, N 9.35%.

EXAMPLE 27

3R-[2-Benzylsulphinyl-2-methyl-1S-(methylcarbamoyl)propylcarbamoyl]-2S-hydroxy-5-methyl-hexanohydroxamic acid

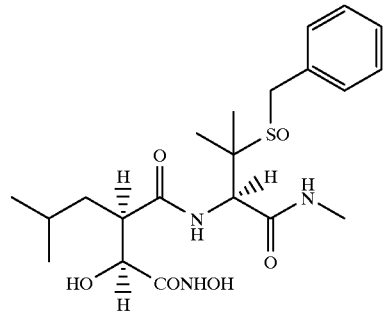

3R-[2-Benzylsulphanylmethyl-2-methyl-1S-(methylcarbamoyl)propylcarbamoyl]-2S-hydroxy-5-methyl-hexanohydroxamic acid (215 mg, 0.49 mmol) was dissolved in methanol (3 ml) and cooled to 0° C. before addition of mCPBA (93 mg, 0.54 mmol). The reaction was allowed to warm to room temperature and stirred for a further 4 hours. The solvent was removed under reduced pressure and the residue was triturated with diethyl ether, filtered, washed with diethyl ether and dried at 60° C. under high vacuum to leave a white solid (142 mg, 63%). m.p. 142–143° C. $^1$H NMR; δ (CH$_3$OD, 330K) (ca. 3:2 mixture of diastereoisomeric sulphoxides), 7.32 (5H, ml, 4.77 (0.6H, s), 4.70 (0.4H, s), 4.09 (2H, m), 3.74 (0.4H, d, J=13.0 Hz), 3.68 (0.6H, d, J=12.6 Hz), 2.82 (1H, m), 2.74 (1.7H, s), 2.73 (1.3H, s), 1.59 (2H, m), 1.47 (1.5H, s), 1.42 (1.5H, s), 1.40 (1.5H, s), 1.36 (1.5H, s), 1.33 (1H, m), 0.88 (3H, d, J=6.5 Hz) and 0.83 (3H, d, J=6.5 Hz). $^{13}$C NMR; δ (CH$_3$OD), 175.9, 175.7, 171.4, 170.4, 133.1, 133.0, 131.6, 131.5, 129.8, 129.7, 129.4, 72.9, 66.0, 62.5, 60.2, 58.7, 56.5, 56.2, 53.4, 39.5, 26.9, 26.4, 23.6, 22.3, 20.1, 18.7, 18.5, 18.1 and 16.9.

EXAMPLE 28

3R-[2-Benzylsulphonyl-2-methyl-1S-(methylcarbamoyl)propylcarbamoyl]-2S-hydroxy-5-methyl-hexanohydroxamic acid

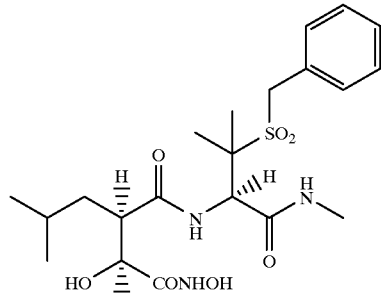

The title compound was prepared by a method analogous to that described in Example 27 using two equivalents of mCPBA.

White solid. m.p. 138.5–139.5° C. $^1$H-NMR; δ (CH$_3$OD), 7.33 (5H, m), 5.06 (1H, s), 4.43 (2H, s), 4.02 (1H, d, J=6.6 Hz), 2.88 (1H, m), 2.71 (3H, s), 1.61 (4H, s and m), 1.46 (4H, s and m), 1.14 (1H, m), 0.89 (3H, d, J=6.4 Hz) and 0.83 (3H, d, J=6.4 Hz). $^{13}$C-NMR; δ (CH$_3$OD), 175.7, 171.3, 170.7, 133.0, 129.6, 129.3, 128.0, 72.9, 65.9, 56.4, 54.9, 39.1, 26.9, 26.3, 23.6, 22.2, 20.0 and 18.6.

The following additional compounds were prepared according to the methods of Example 27 and 28, starting from the appropriate starting materials:

EXAMPLE 29

2S-Hydroxy 3R-[2-(4-methoxybenzylsulphinyl)-2-methyl-1S-(methylcarbamoyl)-propylcarbamoyl]-5-methyl-hexanohydroxamic acid

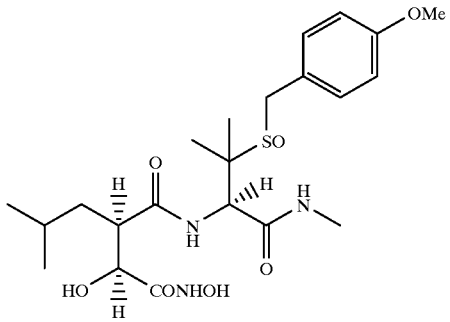

ca. 1:1 mixture of diastereoisomeric sulphoxides

White solid. m.p. 128–129° C. $^1$H NMR; δ (CH$_3$OD), 7.26 (2H, m), 6.88 (2H, m), 4.74 (0.6H, s), 4.68 (0.4H, s), 4.21 (1H, d, J=12.7 Hz), 4.03 (1H, d, J=13.2 Hz), 3.75 (3H, s), 3.68 (0.5H, d, J=12.9 Hz), 3.62 (0.5H, d, J=12.7 Hz), 2.81 (1H, m), 2.71 (3H, d), 1.57 (2H, m), 1.40 (3H, m), 1.34 (4H, m), 0.88 (3H, d, J=6.5 Hz) and 0.83 (3H, d, J=6.5 Hz). $^{13}$C NMR; δ ((CD$_3$)$_2$SO), 172.7, 168.6, 158.9, 131.4, 124.6, 113.9, 71.2, 59.9, 55.1, 51.6, 48.4, 25.3, 23.1, 21.6, 17.9, 16.4 and 15.0.

EXAMPLE 30

2S-Hydroxy 3R-[2-(4-methoxybenzylsulphonyl)-2-methyl-1S-(methylcarbamoyl)-propylcarbamoyl]-5-methyl-hexanohydroxamic acid

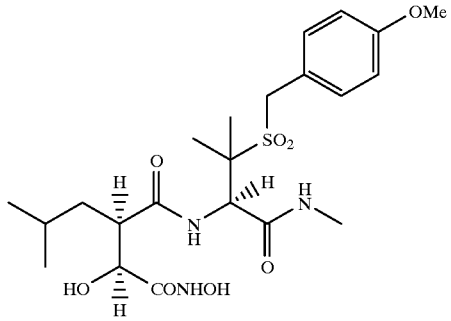

White solid. m.p. 113–114° C. $^1$H NMR; δ (CH$_3$OD), 7.26 (2H, d, J=8.7 Hz), 6.87 (2H, d, J=8.7 Hz), 5.03 (1H, s), 4.36 (2H, s), 4.01 (1H, d, J=6.7 Hz), 3.75 (3H, s), 2.84 (1H, m), 2.70 (3H, s), 1.59 (4H, s and m), 1.45 (4H, s and m), 1.18 (1H, m), 0.88 (3H, d, J=6.4 Hz) and 0.84 (3H, d, J=6.4 Hz). $^{13}$C NMR; δ (CH$_3$OD), 175.9, 171.4, 170.8, 161.6, 134.2, 119.6, 114.9, 73.0, 65.8, 56.5, 55.7, 54.5, 39.2, 26.9, 26.4, 23.7, 22.3, 20.1 and 18.7.

EXAMPLE 31

2S-Hydroxy 3R-[2-methylsulphinyl-2-methyl-1S-(methylcarbamoyl)-propylcarbamoyl]-5-methyl-hexanohydroxamic acid

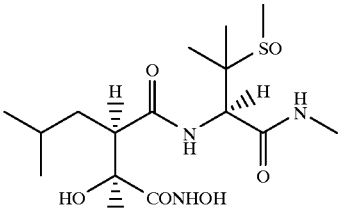

ca. 2:1 mixture of diastereoisomeric sulphoxides

White solid. m.p. 80–81° C. $^1$H NMR; δ (CH$_3$OD), 4.61 (0.4H, S), 4.57 (0.6H, s), 4.06 (1H, m), 2.83 (1H, m), 2.71 (2.1H, s), 2.69 (0.9H, s), 2.50 (1.6H, s), 2.47 (1.4H, s), 1.60 (2H, m), 1.35 (1.5H, s), 1.29 (1.5H, s), 1.27 (1.5H, s), 1.23 (1.5H, s), 1.15 (1H, m) and 0.87 (6H, m). $^{13}$C NMR; δ (CH$_3$OD), 175.7, 171.4, 170.9, 170.3, 66.9, 60.8, 59.3, 58.0, 56.4, 49.3, 49.2, 39.4, 37.3, 32.2, 31.6, 26.9, 26.3, 23.6, 22.4, 19.6, 18.7, 17.9, 17.6, 16.9, 16.2 and 15.4.

EXAMPLE 32

2S-Hydroxy 3R-[2-methylsulphonyl-2-methyl-1S-(methylcarbamoyl)-propylcarbamoyl]-5-methyl-hexanohydroxamic acid

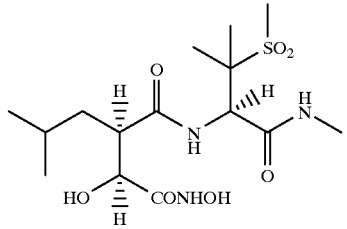

White solid. m.p. 94–96° C. $^1$H-NMR; δ (CH$_3$OD). 4.89 (1H, s), 4.05 (1H, br d), 2.91 (3H, s), 2.83 (1H, m), 2.70 (3H, s), 1.57 (2H, m), 1.52 (3H, s), 1.42 (3H, s), 1.32 (1H, m), 0.87 (3H, d, J=6.3 Hz) and 0.85 (3H, d, J=6.3 Hz). $^{13}$C-NMR; δ (CH$_3$OD), 175.8, 171.4, 170.7, 73.0, 64.9, 56.7, 56.3, 49.5, 39.2, 37.3, 26.9, 26.3, 23.6, 23.4, 22.3, 20.0, 19.7, 19.0 and 18.7.

EXAMPLE 33

3R-[2-Methylsulphinyl-2-methyl-1S-(methylcarbamoyl)propylcarbamoyl]-5-methyl-2S-propen-2-yl-hexanohydroxamic acid

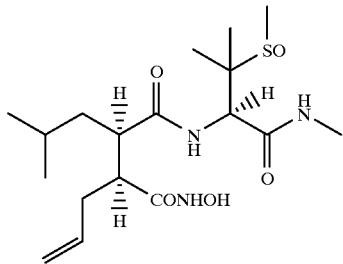

1:1 mixture of diastereomeric sulphoxides

White solid. m.p. 202–204° C. $^1$H-NMR; δ (CH$_3$OD), 5.58 (1H, m), 4.90 (2H, m), 4.68 (0.4H, s), 4.50 (0.6H, s), 2.64 (1.8H, s), 2.62 (1.2H, s), 2.60 (1H, m), 2.54 (1.8H, s), 2.39 (1.2H, s), 2.15 (3H, m), 1.37 (1.8H, s), 1.23 (1.2H, s), 1.20 (1.2H, s), 1.18 (2H, m), 1.15 (1.8H, s), 0.99 (1H, m) and 0.75 (6H, m). $^1$H-NMR; δ (CD$_3$OD), 176. 176.5, 172.1, 170.8, 169.9, 136.1, 135.9, 117.5, 117.4, 61.6, 59.6, 56.8, 56.3, 55.9, 41.6, 41.5, 36.2, 36.1, 35.9, 32.3, 31.2, 27.1, 26.9, 26.2, 24.2, 21.8, 21.7, 17.8 and 15.4. IR (KBr disc), ν$_{max}$, 3254, 3077, 2954, 1634, 1540 cm$^{-1}$. Found: C 52.61, H 8.23, N 10.18%; C$_{18}$H$_{33}$N$_3$O$_5$S.0.4 H$_2$O requires: C 52.64, H 8.29, N 10.23%.

EXAMPLE 34

3R-[2-Methylsulphonyl-2-methyl-1S-(methylcarbamoyl)propylcarbamoyl]-5-methyl-2S-propen-2-yl-hexanohydroxamic acid

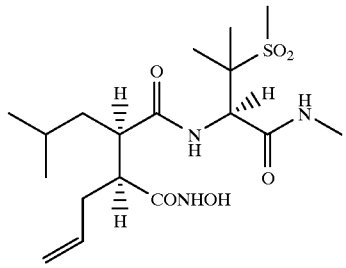

White solid. m.p. 219–221° C. $^1$H-NMR; δ (CD30D), 5.53 (1H, m) 4.93 (2H, m), 4.73 (1H, s), 2.90 (3H, s), 2.60 (3H, s), 2.53 (1H, m), 2.15 (3H, m), 1.46 (3H, s), 1.41 (1H, m), 1.37 (3H, s), 1.26 (1H, m), 1.15 (1H, m), 0.76 (3H, d, J=6.4 Hz) and 0.71 (3H, d, J=6.5 Hz). $^{13}$C-NMR; δ (CD$_3$OD), 176.6, 172.3, 170.3, 136.2, 117.3, 64.4, 55.9, 47.9, 41.7, 36.4, 35.9, 26.9, 26.2, 24.3, 21.8, 20.4 and 17.7. IR (KBr disc); ν$_{max}$, 3270, 3080, 2954, 1662, 1633, 1558, 1540, 1470 cm$^{-1}$. Found: C 50.81, H 7.97, N 9.89%; C$_{18}$H$_{33}$N$_3$O$_6$S.0.3 H$_2$O requires: C 50.88, H 7.97, N 9.89%.

EXAMPLE 35

3R-[2-Benzylsulphinyl-2-methyl-1S-methylcarbamoyl-propylcarbamoyl]-5-methyl-2S-propen-2-yl-hexanohydroxamic acid

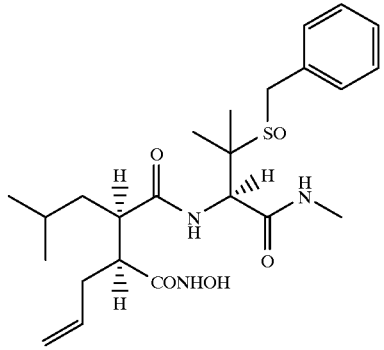

1:1 mixture of diastereomeric sulphoxides

White powder. m.p. 143–144° C. $^1$H-NMR; δ (CD$_3$OD), 7.22 (5H, m), 5.49 (1H, m), 4.78 (3H, br m), 3.56 (0.9H, d, J=12.5 Hz), 3.19 (1.1H, d, J=12.1 Hz), 2.65 (1.5H, s), 2.63 (1.5H, s), 2.62 (1H, m), 2.18–2.06 (3H, br m), 1.42 (2H, m), 1.39 (1.8H, s), 1.36 (1.2H, s), 1.32 (1.2H, s), 1.29 (1.8H, s), 1.08 (1H, m) and 0.74 (6H, m). $^{13}$C-NMR; δ (CH$_3$OD), 176.8, 176.4, 172.1, 170.7, 170.5, 169.9, 135.9, 133.0, 131.7, 130.5, 129.4, 127.9, 118.6, 62.9, 56.9, 53.9, 52.7, 41.8, 41.5, 36.1, 27.2, 27.1, 26.2, 24.2, 21.8, 18.5, 17.6, 16.9 and 16.3. IR (KBr disc); ν$_{max}$, 3277, 3077, 2956, 1645, 1526, 1466, 1412, 1387 cm$^{-1}$. Found: C 57.65, H 7.53, N 8.68%; C$_{24}$H$_{37}$N$_3$O$_5$S.1.1 H$_2$O requires C 57.72, H 7.91, N 8.68%.

EXAMPLE 36

3R-[2-Benzylsulphanyl-2-methyl-1S-(methylcarbamoyl)propylcarbamoyl]-2S-hydroxy-6-phenyl-hexanoic acid

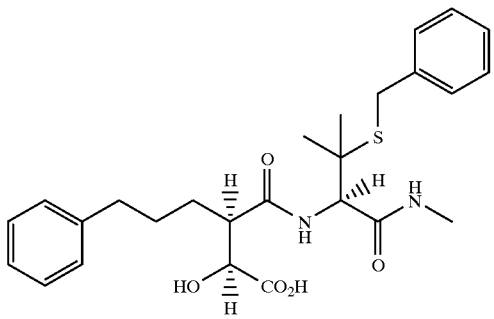

A solution of $N^2$-[2R-(2,2-dimethyl-4-oxo-1,3-dioxalan-5S-yl)-5-phenylpentanoyl]-S-benzyl-L-penicillamine-$N^1$-methylamide (prepared by a method analogous to that described in Example 4) (1.00 g, 1.90 mmol) in THF (15 ml) was cooled to 0° C. and 1M hydrochloric acid (15 ml) was added. The mixture was stirred overnight at room temperature after which TLC analysis indicated that all of the starting material had been consumed. The solvents were removed under reduced pressure to leave a pale yellow foam which was redissolved in ethyl acetate. The solution washed with brine, dried over magnesium sulphate, filtered and evaporated under reduced pressure to afford the title compound as an pale yellow foam (620 mg, 67%; single diastereoisomer). m.p. 73° C. $^1$H-NMR; δ (CDCl$_3$), 7.50 (1H, d, J=8.7 Hz), 7.31–7.12 (11H, m), 6.62 (1H, d, J=4.8 Hz), 4.56 (1H, d, J=8.8 Hz), 4.30 (1H, d, J=2.7 Hz), 3.80 (2H, s), 2.87–2.82 (1H, m), 2.71 (3H, d, J=4.7 Hz), 2.63–2.57 (2H, m), 1.79–1.71 (4H, m), 1.41 (3H, s) and 1.30 (3H, s). $^{13}$C-NMR; δ (CDCl$_3$), 175.0, 174.1, 169.9, 141.5, 137.4, 129.0, 128.5, 128.2, 127.1, 125.8, 70.7, 59.1, 49.5, 48.2, 35.4, 33.2, 29.1, 28.9, 26.2, 26.0, 25.6 and 21.0. Found: C 63.67, H 7.08, N 5.64 %; $C_{26}H_{34}N_2O_5S.0.2\ H_2O$ requires C 63.70, H 7.07, N 5.71%.

We claim:

1. A compound of formula (I)

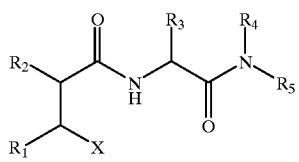

(I)

wherein
$R_1$ is non-aromatic heterocyclyl;
substituted non-aromatic heterocyclyl;
non-aromatic heterocyclyl($C_1$–$C_6$)alkyl-;
substituted non-aromatic heterocyclyl($C_1$–$C_6$)alkyl-;
a group BSO$_n$A- wherein
n is 0, 1 or 2 and
B is hydrogen or a ($C_1$–$C_6$) alkyl, phenyl, substituted phenyl, non-aromatic heterocyclyl, ($C_1$–$C_6$)acyl, phenacyl or substituted phenacyl group, and
A represents ($C_1$–$C_6$)alkylene;
amino;
protected amino;
acylamino;
OH;
SH;
($C_1$–$C_6$)alkoxy;
($C_1$–$C_6$)alkylamino;
di-($C_1$–$C_6$)alkylamino; or
($C_1$–$C_6$)alkylthio;
$R_2$ is a ($C_1$–$C_6$)alkyl, ($C_2$–$C_6$)alkenyl, ($C_2$–$C_6$)alkynyl, phenyl($C_1$–$C_6$)alkyl-, heteroaryl($C_1$–$C_6$)alkyl-, cycloalkyl($C_1$–$C_6$)alkyl- or cycloalkenyl($C_1$–$C_6$)alkyl-group, any one of which may be optionally substituted by one or more substituents selected from ($C_1$–$C_6$)alkyl, —O($C_1$–$C_6$)alkyl, —S($C_1$–$C_6$)alkyl, halo and cyano (—CN);
$R_3$ is a group —CR$_9$R$_{10}$R$_{11}$ in which
$R_9$ and $R_{10}$ are each independently ($C_1$–$C_6$)alkyl, ($C_2$–$C_6$)alkenyl, ($C_2$–$C_6$)alkynyl, phenyl($C_1$–$C_6$)alkyl-, or a group as defined for $R_{11}$ below, or $R_9$ and $R_{10}$ together with the carbon atom to which they are attached form a 3 to 8 membered cycloalkyl or a 5- to 6-membered heterocyclic ring, and
$R_{11}$ is —OH, —SH, or —O($C_1$–$C_6$)alkyl, —O($C_2$–$C_6$)alkenyl, —S($C_1$–$C_6$)alkyl, —SO($C_1$–$C_6$)alkyl, —SO$_2$($C_1$–$C_6$)alkyl, —S($C_2$–$C_6$)alkenyl, —SO($C_2$–$C_6$)alkenyl, —SO$_2$($C_2$–$C_6$)alkenyl or a group —Q—W wherein Q represents —O—, —S—, —SO— or —SO$_2$— and W represents a phenyl, phenylalkyl, ($C_3$–$C_8$)cycloalkyl, ($C_3$–$C_8$)cycloalkylalkyl-, ($C_4$–$C_8$)cycloalkenyl, ($C_4$–$C_8$)cycloalkenylalkyl-, heteroaryl or heteroarylalkyl-group, which group W may optionally be substituted by one or more substituents independently selected from, hydroxyl, halogen, —CN, —CO$_2$H, —CO$_2$($C_1$–$C_6$)alkyl, —CONH$_2$, —CONH($C_1$–$C_6$)alkyl, —CONH($C_1$–$C_6$alkyl)$_2$, —CHO, —CH$_2$OH, ($C_1$–$C_4$)perfluoroalkyl, —O($C_1$–$C_6$)alkyl, —S($C_1$–$C_6$)alkyl, —SO($C_1$–$C_6$)alkyl, —SO$_2$($C_1$–$C_6$)alkyl, —NO$_2$, —NH$_2$, —NH($C_1$–$C_6$)alkyl, —N(($C_1$–$C_6$)alkyl)$_2$, —NHCO($C_1$–$C_6$)alkyl, ($C_1$–$C_6$)alkyl, ($C_2$–$C_6$)alkenyl, ($C_2$–$C_6$)alkyn ($C_3$–$C_8$)cycloalkyl, ($C_4$–$C_8$)cycloalkenyl, phenyl or benzyl;
X is a —CO$_2$H or —CONHOH group;
$R_4$ is hydrogen, ($C_1$–$C_6$)alkyl, ($C_1$–$C_4$)perfluoroalkyl or a group D-($C_1$–$C_6$)alkyl- wherein D represents hydroxy, ($C_1$–$C_6$)alkoxy, ($C_1$–$C_6$)alkylsulphanyl-, acylamino, optionally substituted phenyl or heteroaryl, —NH$_2$, or mono- or di-($C_1$–$C_6$)alkyl amino;
or a salt, hydrate or solvate thereof.

2. A compound of formula (I)

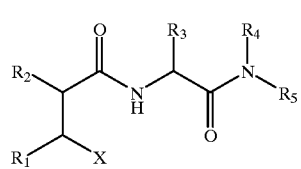

(I)

wherein
$R_1$ is hydrogen;
($C_1$–$C_6$)alkyl;
($C_2$–$C_6$)alkenyl;
phenyl;
substituted phenyl;
phenyl ($C_1$–$C_6$)alkyl)-;
heterocyclyl, except non-aromatic heterocyclyl;

substituted heterocyclyl, except non-aromatic substituted heterocyclyl;
heterocyclyl($C_1$–$C_6$)alkyl-, except non-aromatic heterocyclyl($C_1$–$C_6$)alkyl-;
substituted heterocyclyl($C_1$–$C_6$)alkyl-, except non-aromatic substituted heterocyclyl($C_1$–$C_6$)alkyl-;
aryl ($C_1$–$C_6$)alkyl-;
amino($C_1$–$C_6$)alkyl-, hydroxy($C_1$–$C_6$)alkyl-, mercapto ($C_1$–$C_6$)alkyl- or carboxy($C_1$–$C_6$)alkyl- wherein the amino-, hydroxy-, mercapto- or carboxyl- group are optionally-protected or the carboxyl- group amidated; or
lower alkyl substituted by carbamoyl, mono(lower alkyl)carbamoyl, di(lower alkyl)carbamoyl, di(lower alkyl)amino, or carboxy-lower alkanoylamino;

$R_2$ is a ($C_1$–$C_6$)alkyl, ($C_2$–$C_8$)alkenyl, ($C_2$–$C_6$)alkynyl, phenyl($C_1$–$C_6$)alkyl-, heteroaryl($C_1$–$C_6$)alkyl-, cycloalkyl($C_1$–$C_6$)alkyl- or cycloalkenyl($C_1$–$C_6$)alkyl- group, any one of which may be optionally substituted by one or more substituents selected from ($C_1$–$C_6$) alkyl, —O($C_1$–$C_6$)alkyl, and —S($C_1$–$C_6$)alkyl-;

$R_3$ a group —$CR_9R_{10}R_{11}$ in which
$R_9$ and $R_{10}$ together with the carbon atom to which they are attached form a 3 to 8 membered cycloalkyl or a 3- to 8-membered heterocyclic ring,
$R_{11}$ is —OH, —SH, —O($C_1$–$C_6$)alkyl, —O($C_2$–$C_6$) alkenyl, or —S($C_1$–$C_6$)alkyl;

X is a —$CO_2H$ or —CONHOH group;

$R_4$ is hydrogen, ($C_1$–$C_6$)alkyl, ($C_1$–$C_4$)perfluoroalkyl or a group D-($C_1$–$C_6$)alkyl- wherein D represents hydroxy, ($C_1$–$C_6$)alkoxy, ($C_1$–$C_6$)alkylsulphanyl-, acylamino, optionally substituted phenyl or heteroaryl, —$NH_2$, or mono- or di-($C_1$–$C_6$)alkyl amino;

$R_5$ is hydrogen or a ($C_1$–$C_6$)alkyl group;
or a salt, hydrate or solvate thereof.

3. A compound as claimed in claim 1 or 2, wherein the stereochemistry is as follows:
C atom carrying the $R_1$ and X groups —S,
C atom carrying the $R_2$ group —R,
C atom carrying the $R_3$ group —S.

4. A compound as claimed in claim 3, wherein $R_1$ is hydrogen, methyl, ethyl, hydroxyl, allyl, thienylsulphanylmethyl, thienylsulphinylmethyl, thienylsulphonylmethyl or phthalimidomethyl.

5. A compound as claimed in claim 4, wherein $R_2$ is iso-butyl, n-pentyl, n-hexyl, n-heptyl, n-octyl, n-nonyl, n-decyl, or propylsulphanyl, cyclohexylpropyl, phenylpropyl, 4-chlorophenylpropyl, 4-methylphenylpropyl, 4-methoxyphenylpropyl, or phenylbutyl.

6. A compound as claimed in claim 5, wherein $R_3$ is:
—C($C_1$–$C_6$ alkyl)$_3$;
—CH($C_1$–$C_4$ perfluoroalkyl)$_2$;
—C($C_1$–$C_4$ perfluoroalkyl)$_3$;
—C($C_1$–$C_6$ alkyl)$_2R_{11}$ or a 3 to 8 membered cycloalkyl group substituted by ($C_1$–$C_6$)alkyl or $R_{11}$ at the α-position, wherein
$R_{11}$ is —OH, —SH, halogen, ($C_1$–$C_4$)perfluoroalkyl, —$CH_2OH$,
—$CO_2H$, —$CO_2$($C_1$–$C_6$)alkyl, optionally substituted phenyl or
optionally substituted heteroaryl, —O($C_1$–$C_6$)alkyl, —S($C_1$–$C_6$)alkyl,
—SO($C_1$–$C_6$)alkyl, —$SO_2$($C_1$–$C_6$) alkyl, OPh, —$OCH_2Ph$, —SPh,
—SOPh, —$SO_2Ph$, —$SCH_2Ph$, —$SOCH_2Ph$, —$SO_2CH_2Ph$, cyclohexylmethylsulphanyl, cyclohexylmethylsulphinyl, cyclohexylmethylsulphonyl, in which any of the foregoing Ph (phenyl) or cyclohexyl groups may be substituted, for example by —OH, —O($C_1$–$C_6$)alkyl or halogen.

7. A compound as claimed in claim 6, wherein $R_3$ is 1,1-diethylprop-1-yl, 1-cyclopropylethyl, adamant-1-yl, 2-fluoroprop-2-yl, 1,1,1,3,3,3,-hexafluoroprop-2yl, 2-carboxyprop-2-yl, 2-methoxycarbonylprop-2-yl, 2-(tetrahydropyran-4-yl)prop-2-yl, 2-(tetrahydrofuran-2-yl) prop-2-yl, diphenylmethyl or 2-phenylprop-2-yl, 2-hydroxyprop-2-yl, 2-mercaptoprop-2-yl, 2-methoxyprop-2-yl, 2-(2-methoxyethoxymethoxy)prop-2-yl, 2-methylsulphanylprop-2-yl, 2-methylsulphinylprop-2-yl, 2-methylsulphonylprop-2-yl, 2-benzylsulphanylprop-2-yl, 2-benzylsulphinylprop-2-yl, 2-benzylsulphonylprop-2-yl, 2-(4-methoxybenzylsulphanyl)prop-2-yl, 2-(4-methoxybenzylsulphinyl)prop-2-yl, 2-(4-methoxybenzylsulphonyl)prop-2-yl, 2-cyclohexylmethylsulphanyl-prop-2-yl, cyclohexylmethylsulphinyl-prop-2-yl, cyclohexylmethylsulphanyl-prop-2-yl, or 1-hydroxycyclopent-1-yl.

8. A compound as claimed in claim 7, wherein $R_4$ is $C_1$–$C_6$ alkyl, ($C_1$–$C_4$)perfluoroalkyl or a group D-($C_1$–$C_6$ alkyl) wherein D represents hydroxy, ($C_1$–$C_6$)alkoxy, ($C_1$–$C_6$)alkylthio, acylamino, optionally substituted phenyl or heteroaryl.

9. A compound as claimed in claim 8, wherein $R_4$ is methyl, ethyl, propyl, n-butyl, t-butyl, hydroxyethyl, hydroxypropyl, 2,2dimethyl-3-hydroxypropyl, hydroxybutyl, methoxyethyl, ethoxyethyl, methoxypropyl, 2,2-dimethyl-3-methoxypropyl, 2,2-dimethyl-3ethoxypropyl, 2-ethylthioethyl, 2-acetoxyethyl, N-acetyl-aminoethyl, 3-(2-pyrrolidone)propyl, optionally substituted phenylethyl, phenylpropyl, phenylbutyl or phenylpentyl.

10. A compound as claimed in claim 9, wherein $R_5$ is hydrogen.

11. A compound selected from the group consisting of
2S-Hydroxy-3R-[2-(4-methoxybenzylsulphinyl)-2-methyl-1S-(methylcarbamoyl)-propylcarbamoyl]-5-methyl-hexanohydroxamic acid,
2S-Hydroxy-3R-[1S-(methylcarbamoyl)-2-benzylsulphanyl-2-methylpropylcarbamoyl]-5-methyl-hexanohydroxamic acid,
2S-Hydroxy-3R-[2-methylthio-2-methyl-1S-(methylcarbamoyl)propylcarbamoyl]-5-methyl-hexanohydroxamic acid,
3R-[2-Benzylsulphanyl-2-methyl-1S-(methylcarbamoyl) propylcarbamoyl]-2S-hydroxy-6-phenyl-hexanohydroxamic acid,
2S-Hydroxy-3R-[1S-(methylcarbamoyl)-2-fluoro-2-methyl-propylcarbamoyl]-5-methyl-hexanohydroxamic acid,
3R-[2-Benzylsulphinyl-2-methyl-1S-(methylcarbamoyl) propylcarbamoyl]-2S-hydroxy-6-phenyl-hexanohydroxamic acid,
3R-[2-Cyclohexylmethylsulphanyl-2-methyl-1S-(methylcarbamoyl)propylcarbamoyl]-2S-hydroxy-6-phenyl-hexanohydroxamic acid,
and salts, solvates or hydrates thereof.

12. A compound selected from the group consisting of
3R-[1S-(Methylcarbamoyl)-2-benzylsulphanyl-2-methyl-propylcarbamoyl]-5-methyl-hexanohydroxamic acid, 3R-[1S-Benzylcarbamoyl-(1-methylcyclopropyl)methylcarbamoyl]-5-methyl-hexanohydroxamic acid, 3R-[2-Benzylsulphanyl-1S-(methylcarbamoyl)-2-methyl-propylcarbamoyl]-6-phenyl-hexanohydroxamic acid, 2S-Hydroxy-3R-[2-(4-methoxybenzylsulphanyl)-2-methyl-1S-(methylcarbamoyl)-propylcarbamoyl]-5-methyl-hexanohydroxamic acid, 2S-Hydroxy-3R-[1S-(methylcarbamoyl)-2-trifluoromethyl-3,3,3-trifluoropropylcarbamoyl]-5-methyl-hexanohydroxamic acid, 3R-[2,2-diphenyl-1S-(methylcarbamoyl)ethylcarbamoyl]-2S-hydroxy-5-methyl-hexanohydroxamic acid, 2S-Hydroxy-3R-[2-hydroxy-1R or S-(methylcarbamoyl)-2-methylpropylcarbamoyl]-5-methyl-hexanohydroxamic acid, 2S-Hydroxy-3R-[2,2-diethyl-1S-(methylcarbamoyl)-butylcarbamoyl]-5-methyl-hexanohydroxamic acid, 2S-Hydroxy-3R-[1S-methylcarbamoyl-2-methyl-2-phenylpropylcarbamoyl]-5-methyl-hexanohydroxamic acid, 2S-Hydroxy-3R-[1S-tert-butylcarbamoyl-2-benzylsulphanyl-2-methylpropylcarbamoyl]-5-methyl-hexanohydroxamic acid, 2S-Hydroxy-3R-[1S-(methylcarbamoyl)-2-mercapto-2-methyl-propylcarbamoyl]-5-methyl-hexanohydroxamic acid, 2S-Hydroxy-3R-[1S-(methylcarbamoyl)-1-adamant-1-yl-methylcarbamoyl]-5-methyl-hexanohydroxamic acid, 2S-Hydroxy-3R-[2-methoxy-1S-(methylcarbamoyl)-2-methyl-propylcarbamoyl]-5-methyl-hexanohydroxamic acid, 2S-Hydroxy-3R-[2-methoxycarbonyl-1S-(methylcarbamoyl)-2-methylhexanohydroxamic acid, 3R-[2-methylthio-2-methyl-1S-(methylcarbamoyl)propylcarbamoyl-5-methyl-2S-propen-2-yl-hexanohydroxamic acid, 3R-[2,2-Diphenyl-1S-(methylcarbamoyl)-propylcarbamoyl]-5-methyl-2S-propen-2-yl-hexanohydroxamic acid, 3R-[2-Benzylsulphanyl-2-methyl-1S-(methylcarbamoyl)propylcarbamoyl]-5-methyl-2S-phthalimidomethyl-hexanohydroxamic acid, 3R-[2-Benzylsulphonyl-2-methyl-1S-(methylcarbamoyl)propylcarbamoyl]-2S-hydroxy-5-methyl-hexanohydroxamic acid, 2S-Hydroxy-3R-[2-(4-methoxybenzylsulphonyl)-2-methyl-1S-(methylcarbamoyl)-propylcarbamoyl-5-methyl-hexanohydroxamic acid, 2S-Hydroxy-3R-[2-methylsulphinyl-2-methyl-1S-(methylcarbamoyl)-propylcarbamoyl-5-methyl-hexanohydroxamic acid, 2S-Hydroxy-3R-[2-methylsulphonyl-2-methyl-1S-(methylcarbamoyl)-propylcarbamoyl-5-methyl-hexanohydroxamic acid, 3R-[2-Benzylsulphinyl-2-methyl-1S-(methylcarbamoyl)propylcarbamoyl]-5-methyl-2S-propen-2-yl-hexanohydroxamic acid, 3R-[2,2-Diethyl-1S-(methylcarbamoyl)-butylcarbamoyl]-5-methyl-2S-propen-2-yl-hexanohydroxamic acid, 3R-[2-Benzylsulphanyl-2-methyl-1S-(methylcarbamoyl)propylcarbamoyl]-2S-hydroxy-6-phenyl-hexanoic acid, and salts, solvates or hydrates thereof.

13. A pharmaceutical composition comprising the compound of claim 1 or 2 and a pharmaceutically or veterinarily acceptable excipient or carrier.

14. The pharmaceutical composition of claim 13 wherein said pharmaceutical composition is administered orally.

15. A method of inhibiting MMP activity comprising administering an effective amount of the compound of claim 1 or 2.

16. The method of claim 15, wherein said MMP activity is the result of a patient suffering from, or as a prophylaxis for, rheumatoid arthritis, osteoarthritis, periodontists, gingivitis, corneal ulceration or tumor invasion by secondary metastases.

17. A pharmaceutical composition comprising the compound of any of claims 11 or 12 and a pharmaceutically or veterinarily acceptable excipient or carrier.

18. The pharmaceutical composition of claim 17, wherein said pharmaceutical composition is administered orally.

19. A method of inhibiting MMP activity comprising administering an effective amount of the compound of any of claims 11 or 12.

20. The method of claim 19, wherein said MMP activity is the result of a patient suffering from, or as a prophylaxis for, rheumatoid arthritis, osteoarthritis, periodontists, gingivitis, corneal ulceration or tumor invasion by secondary metastases.

* * * * *

UNITED STATES PATENT AND TRADEMARK OFFICE
CERTIFICATE OF CORRECTION

PATENT NO. : 5,902,791

DATED : May 11, 1999

INVENTOR(S) : Raymond Paul Beckett, et al.

It is certified that error appears in the above-identified patent and that said Letters Patent is hereby corrected as shown below:

Column 44, lines 55-57, delete "2S-Hydroxy-3R-[1S-(methylcarbamoyl)-2-fluoro-2-methyl-propylcarbamoyl]-5-methyl-hexanohydroxamic acid,"

Column 45, lines 9-11, delete "2S-Hydroxy-3R-[1S-(methylcarbamoyl)-2-trifluoromethyl-3,3,3-trifluoro-propylcarbamoyl]-5-methyl-hexanohydroxamic acid,"

Column 45, lines 12-14, delete "3R-[2,2-diphenyl-1S-(methylcarbamoyl)ethylcarbamoyl]-2S-Hydroxy-5-methyl-hexanohydroxamic acid,"

Column 45, lines 21-23, delete "2S-Hydroxy-3R-[1S-(methylcarbamoyl)-2-methyl-2-phenylpropylcarbamoyl]-5-methyl-hexanohydroxamic acid,"

Column 45, lines 36 and 37, delete "2S- Hydroxy-3R-[2-methoxycarbonyl-1S-(methylcarbamoyl)-2-methyl-hexanohydroxamic acid,"

UNITED STATES PATENT AND TRADEMARK OFFICE
CERTIFICATE OF CORRECTION

PATENT NO. : 5,902,791

DATED : May 11, 1999

INVENTOR(S) : Raymond Paul Beckett, et al.

It is certified that error appears in the above-identified patent and that said Letters Patent is hereby corrected as shown below:

Column 45, lines 42-44, delete "3R-[2,2-Diphenyl-1S-(methylcarbamoyl)-propylcarbamoyl]-5-methyl-2S-propen-2-yl-hexanohydroxamic acid,"

Signed and Sealed this

Seventh Day of September, 1999

Attest:

Q. TODD DICKINSON

Attesting Officer

Acting Commissioner of Patents and Trademarks